(12) United States Patent
Geilen et al.

(10) Patent No.: US 9,914,681 B2
(45) Date of Patent: Mar. 13, 2018

(54) PREPARATION OF HIGH-QUALITY OXO PROCESS ALCOHOLS FROM INCONSTANT RAW MATERIAL SOURCES

(71) Applicants: Frank Geilen, Haltern am See (DE); Katrin Marie Dyballa, Recklinghausen (DE); Dieter Hess, Marl (DE); Stephan Peitz, Oer-Erkenschwick (DE); Robert Franke, Marl (DE); Dirk Fridag, Haltern am See (DE); Dietrich Maschmeyer, Recklinghausen (DE); Helene Reeker, Dortmund (DE); Guido Stochniol, Haltern am See (DE)

(72) Inventors: Frank Geilen, Haltern am See (DE); Katrin Marie Dyballa, Recklinghausen (DE); Dieter Hess, Marl (DE); Stephan Peitz, Oer-Erkenschwick (DE); Robert Franke, Marl (DE); Dirk Fridag, Haltern am See (DE); Dietrich Maschmeyer, Recklinghausen (DE); Helene Reeker, Dortmund (DE); Guido Stochniol, Haltern am See (DE)

(73) Assignee: Evonik Degussa GmbH, Essen (DE)

( * ) Notice: Subject to any disclaimer, the term of this patent is extended or adjusted under 35 U.S.C. 154(b) by 183 days.

(21) Appl. No.: 14/717,183

(22) Filed: May 20, 2015

(65) Prior Publication Data

US 2015/0336861 A1    Nov. 26, 2015

(30) Foreign Application Priority Data

May 20, 2014   (DE) .................. 10 2014 209 536

(51) Int. Cl.
*C07C 29/14*   (2006.01)
*C07C 45/50*   (2006.01)
(Continued)

(52) U.S. Cl.
CPC ............. *C07C 29/14* (2013.01); *B01J 31/185* (2013.01); *B01J 31/1885* (2013.01); *C07C 2/24* (2013.01);
(Continued)

(58) Field of Classification Search
CPC ..................... C07C 2/04–2/36; C07C 45/50
See application file for complete search history.

(56) References Cited

U.S. PATENT DOCUMENTS 6,015,928 A     1/2000   Gubisch et al.
6,403,837 B1 *  6/2002   Hess .................. C07C 45/50
                                                568/451
(Continued)

FOREIGN PATENT DOCUMENTS

DE        10015002 A1     9/2001
DE     102008007080 A1    8/2009
(Continued)

OTHER PUBLICATIONS

Extended European Search Report dated Oct. 20, 2015 in Patent Application No. 15168100.4.
(Continued)

*Primary Examiner* — Medhanit W Bahta
(74) *Attorney, Agent, or Firm* — Oblon, McClelland, Maier & Neustadt, L.L.P.

(57) ABSTRACT

The preparation of high-quality oxo process alcohols from inconstant raw material sources is the technically demanding problem which is addressed by a process for continuously preparing an alcohol mixture, in which an input mixture which contains an olefin and has a composition that changes over time is subjected to an oligomerization to obtain an oligomerizate and at least a portion of the olefin oligomers present in the oligomerizate are hydroformylated with carbon monoxide and hydrogen in a hydroformylation in the (Continued)

presence of a homogeneous catalyst system to give aldehydes, at least some of which are converted to the alcohol mixture by subsequent hydrogenation. The process provides a constant plasticizer quality to be produced over a long production period and, optionally, a higher throughput with the same product quality. This is achieved a) by control of the temperature and/or the conversion of the oligomerization as a function of the current composition of the oligomerizate; and b) by control of the composition of the catalyst system and/or of the pressure of the hydroformylation as a function of the current composition of the aldehydes.

19 Claims, 5 Drawing Sheets

(51) Int. Cl.

| | | |
|---|---|---|
| C07C 2/24 | (2006.01) | |
| C07C 67/08 | (2006.01) | |
| C07C 69/80 | (2006.01) | |
| C08K 5/12 | (2006.01) | |
| B01J 31/18 | (2006.01) | |
| C07C 29/141 | (2006.01) | |

(52) U.S. Cl.
CPC ............ *C07C 29/141* (2013.01); *C07C 45/50* (2013.01); *C07C 67/08* (2013.01); *C07C 69/80* (2013.01); *C08K 5/12* (2013.01); *C07C 2523/755* (2013.01)

(56) References Cited

U.S. PATENT DOCUMENTS

| | | | |
|---|---|---|---|
| 6,482,992 B2* | 11/2002 | Scholz | C07C 29/16 568/451 |
| 7,323,586 B2* | 1/2008 | Wiese | C07C 69/80 106/316 |
| 9,272,973 B2* | 3/2016 | Fridag | B01J 31/0209 |
| 9,682,898 B2* | 6/2017 | Peitz | C07C 2/08 |
| 2004/0238787 A1 | 12/2004 | Wiese et al. | |
| 2011/0301398 A1* | 12/2011 | Heidemann | C07C 2/10 585/512 |
| 2012/0253080 A1 | 10/2012 | Eisenschmid et al. | |
| 2013/0030233 A1* | 1/2013 | Boeing | B01J 31/0281 585/511 |

FOREIGN PATENT DOCUMENTS

| | | |
|---|---|---|
| DE | 102008007081 A1 | 8/2009 |
| DE | 102013212481 A1 | 12/2014 |
| EP | 0 850 905 A1 | 7/1998 |
| EP | 1029839 A1 | 8/2000 |
| EP | 1099678 A1 | 5/2001 |
| EP | 1430014 B1 | 6/2004 |
| EP | 1674441 A1 | 6/2006 |
| EP | 2220017 B1 | 8/2010 |
| WO | 9925668 A1 | 5/1999 |
| WO | WO 03/029180 A1 | 4/2003 |
| WO | 2011000697 A1 | 1/2011 |

OTHER PUBLICATIONS

Franke, et. al., "Applied Hydroformylation", Chemical Reviews ACS Publications, 2012 American Chemical Society, Aug. 2012, pp. 5675-5732.
Frohning, et. al., "Carbon Monoxide and Synthesis Gas Chemistry", Chapter 2.1, pp. 29-92.
Haymore, et. al., "Regioselectivity in Hydroformylation of Linear and Branched Octenes Using HCO(CO)$_4$", Corporate Research Laboratories, Annals New York Academy of Sciences, pp. 159-175.
Keim W., "Katalytisches Cracken and $C_4$-Chemie", Tagungsberichte, Apr. 1989, p. 326.
Friedlander, et. al., "Make Plasticizer Olefins Via N-Butene Dimerization", Hydrocarbon Processing, Feb. 1986, pp. 31-33.
Nierlich, F., "Oligomerize for Better Gasoline", Clean Fuels Technology—Hydrocarbon Processing, Feb. 1992, pp. 45-46.
Tricas, et. al., "Bulky monophosphate ligands for ethane hydroformylation", Journal of Catalysis 298, 2013, pp. 198-205.
Sanfilippo, et. al., "Hydrogenation and Dehydrogenation", Ullmann's Encyclopedia or Industrial Chemistry, vol. 18, 2011, pp. 451-471.
Wilson, A., "Plasticisers: Principles and Practices", London: Institute of Materials, 1995, pp. 135-136.
Wadey, et. al., "The Nonyl Phthalate Ester and Its Use in Flexible PVC", Journal of Vinyl Technology, vol. 12, Dec. 1990, pp. 208-211.
Kamer, et. al., "Rhodium Catalyzed Hydroformylation, Chapter 3.3 Diphosphites", Catalysis by Metal Complexes, Apr. 2006, pp. 44-48.
Falbe, et. al., "Alcohols, Aliphatic", Ullmann's Encyclopedia or Industrial Chemistry. vol. 2, 2011, pp. 235-261.

* cited by examiner

PREPARATION OF HIGH-QUALITY OXO PROCESS ALCOHOLS FROM INCONSTANT RAW MATERIAL SOURCES

BACKGROUND OF THE INVENTION

Field of the Invention

The invention relates to a process for continuously preparing an alcohol mixture, in which an input mixture which comprises an olefin and has a composition that changes over time is subjected to an oligomerization to obtain an oligomerizate and at least a portion of the olefin oligomers present in the oligomerizate are hydroformylated with carbon monoxide and hydrogen in a hydroformylation in the presence of a homogeneous catalyst system to give an aldehyde, at least some of which is converted to the alcohol mixture by subsequent hydrogenation.

Discussion of the Background

Hydroformylation—also called the oxo process—enables reaction of olefins (alkenes) with synthesis gas (mixture of carbon monoxide and hydrogen) to give aldehydes. The aldehydes obtained then correspondingly have one carbon atom more than the olefins used. Subsequent hydrogenation of the aldehydes gives rise to alcohols, which are also called "oxo alcohols" because of their genesis.

In principle, all olefins are amenable to hydroformylation, but in practice the substrates used in the hydroformylation are usually those olefins having two to 20 carbon atoms. Since oxo process alcohols can be used in a variety of ways—for instance for the production of plasticizers for PVC, as detergents in washing compositions and as odorants—hydroformylation is practiced on the industrial scale.

A good overview of the general state of hydroformylation of olefins can be found in B. CORNILS, W. A. HERRMANN, "Applied Homogeneous Catalysis with Organometallic Compounds", vol. 1 & 2, VCH, Weinheim, N.Y., 1996 and in

R. Franke, D. Selent, A. Börner, "Applied Hydroformylation", Chem. Rev., 2012 (112), p. 5675-5732, DOI: 10.1021/cr3001803.

One example of an oxo process alcohol for which there is a high global demand is isononanol, INA for short. Isononanol is a mixture of isomeric nonyl alcohols, for example n-nonanol, and singly and/or multiply branched nonanols, such as methyloctanol in particular. INA has the CAS No. 27458-94-2 and is used essentially in plasticizer production. The $C_9$ oxo process alcohol INA is obtained by hydroformylation of $C_8$ olefins, for example 1-octene, to the corresponding $C_9$ aldehydes and the subsequent hydrogenation thereof.

The patent literature contains detailed process descriptions for preparation of INA: For instance, DE102008007080A1 and EP2220017B1 disclose Co-based processes for preparing INA. EP1674441B1 discloses a two-stage INA process in which a Co-catalyzed hydroformylation is followed by an Rh-catalyzed oxo reaction.

Important criteria for distinction of industrial hydroformylation processes, as well as the substrate used, are the catalyst system, the phase division in the reactor and the technique for discharge of the reaction products from the reactor. A further aspect of industrial relevance is the number of reaction stages conducted.

In industry, either cobalt- or rhodium-based catalyst systems are used, the latter being complexed with organophosphorus ligands such as phosphine, phosphite, phosphoramidite or phosphonite ligands, in each case with trivalent phosphorus. These catalyst systems are present in the reaction mixture in homogeneously dissolved form.

The type of catalyst system and the optimal reaction conditions for the hydroformylation are dependent on the reactivity of the olefin used. The different reactivity of isomeric $C_8$ olefins is described in:

B. L. Haymore, A. van Hasselt, R. Beck, Annals of the New York Acad. Sci., 415, 1983, p. 159-175

The products of the hydroformylation are determined by the structure of the input olefins, the catalyst system and the reaction conditions. If the aim is to obtain alcohols as conversion products of the oxo process for the production of detergents and plasticizers, the oxo reaction should produce very substantially linear aldehydes. The products synthesized therefrom have particularly advantageous properties, for example low viscosities of the resulting plasticizers.

The structure of the input olefins is highly dependent on their origin. Thus, different $C_8$ olefins are useful for preparation of $C_9$ aldehydes: In the simplest case, 1-octene is used, which can be prepared, for example, by oligomerization of ethylene (see below) or alongside other olefins by a Fischer-Tropsch process. 1-Octene obtained in another way is always accompanied by a large number of structurally isomeric $C_8$ olefins. From this point of view, it is not the case that a single olefin is hydroformylated; instead, an input mixture comprising a multitude of isomeric olefins is used.

A mixture of $C_8$ olefins having a defined number of isomers can be obtained by the oligomerization of $C_2$ or $C_4$ olefins:

Oligomerization is understood to mean the reaction of hydrocarbons with themselves, forming correspondingly longer-chain hydrocarbons. For example, the oligomerization of two olefins having three carbon atoms (dimerization) can form an olefin having six carbon atoms. If, in contrast, three olefins having three carbon atoms are joined to one another (trimerization), the result is an olefin having nine carbon atoms.

If butenes—i.e. what are called $C_4$ olefins having four carbon atoms—are subjected to an oligomerization, the result is essentially olefins having eight carbon atoms (often called "dibutenes"), olefins having twelve carbon atoms ($C_{12}$ olefins, "tributenes") and, to a smaller extent, olefins having more than twelve carbon atoms ($C_{12+}$ olefins). For industrial purposes, a distinction is made between what are called di-n-butenes, i.e. isomeric $C_8$ olefins which are prepared from mixtures of 1-butene and/or 2-butenes, and what are called diisobutenes, which are obtained by dimerization of isobutene and have a higher level of branching.

Di-n-butenes, i.e. mixtures of $C_8$ olefins which result from oligomerization of linear butenes, are of much better suitability for the preparation of highly linear oxo process alcohols than diisobutenes, since they have a much lower level of branching.

An even lower level of branching is possessed by $C_8$ olefin mixtures which are obtained by oligomerization of the $C_2$ olefin ethene. Ethene forms in the cracking of naphtha, but is required in large volumes for production of polyethylene and is consequently a comparatively costly raw material. Consequently, the preparation of $C_8$ olefins from ethene is not always economically viable, even though high-value oxo process alcohols can be produced therefrom.

Much less expensive than ethene are the $C_4$ olefin mixtures which likewise form in the cracking of naphtha (called crack-$C_4$). The preparation of $C_9$ alcohols from these raw materials by the route of the oligomerization and subsequent hydroformylation and hydrogenation is of economic interest if it is possible to prepare sufficiently linear isononanol from an inexpensive $C_4$ mixture of inferior quality.

Another process practiced in industry for oligomerization of $C_4$ olefins is called the "OCTOL process". Detailed description thereof can be found in the non-patent literature, for example in:

B. Scholz: The HÜLS OCTOL Process: Heterogeneously catalyzed dimerization of n-butenes and other olefins. DGMK-Tagung [Meeting of the German Society for Petroleum and Coal Science and Technology] in Karlsruhe, published in Erdol, Erdgas, Kohle, April 1989, pages 21 and 22.

R. H. Friedlander, D. J. Ward, F. Obenaus, F. Nierlich, J. Neumeister: Make plasticizer olefins via n-butene dimerization. Hydrocarbon Processing, February 1986, pages 31 to 33.

F. Nierlich: Oligomerize for better gasoline. Hydrocarbon Processing, February 1992, pages 45 to 46.

Within the patent literature, DE102008007081A1, for example, describes an oligomerization based on the OCTOL process. EP1029839A1 is concerned with the fractionation of the $C_8$ olefins formed in the OCTOL process.

The OCTOL process is generally conducted in a plurality of stages with the aid of a reactor cascade comprising a number of series-connected reaction zones or reactors corresponding to the number of stages. Between each of the individual reaction zones is provided a distillation column which removes the oligomers previously formed from the unconverted butenes in the oligomerizate and discharges them. The unconverted butenes are partly recycled into the upstream oligomerization, and the rest are fed to the downstream oligomerization.

A further multistage process for oligomerization of $C_4$ olefins is known from WO99/25668 or from DE10015002A1. Here, dilution of the olefin streams provided by recycled butanes is practiced, in order to simplify the removal of heat from the exothermic reaction via the reactor output.

According to the manner in which the individual n-butene molecules are joined in the course of the oligomerization, an oligomerizate with a different level of branching is obtained. The level of branching is described by the iso index, which states the mean number of methyl groups per $C_8$ molecule in the isomer mixture.

The iso index for dibutene is defined in formula (1):

$$\text{Iso index} = (\text{proportion by weight of methylheptenes} + 2*\text{proportion by weight of dimethylhexenes})/100 \quad (1)$$

Thus, n-octenes contribute 0, methylheptenes contribute 1 and dimethylhexenes contribute 2 to the iso index of a product mixture of $C_8$ olefins. The lower the iso index, the less branched the structure of the molecules within the mixture.

For the properties of the plasticizer, the level of branching of the olefinic starting mixture which is used for the preparation of the plasticizer alcohol plays a crucial role: the higher the linearity of the $C_8$ olefin mixture, the better the properties of the $C_9$ plasticizer alcohol prepared therefrom. The aim in the preparation of dibutene as starting material for plasticizer alcohols is thus to run the oligomerization so as to obtain a $C_8$ product mixture having a minimum iso index.

For example, in EP1029839A1, the fractionation of the oligomers is set up such that the $C_8$ product mixture removed has a minimum iso index.

WO99/25668A1 achieves a low iso index in another way, by recycling such amounts of the butane removed from the oligomer and of unconverted butene into the oligomerization that the maximum content of oligomers in the converted reaction mixture does not exceed 25% by weight anywhere in the reactor cascade.

Each process utilized a "raffinate II" having a high proportion of 1-butene as starting mixture for the oligomerization. "Raffinate II" is commonly understood to mean a butane/butene mixture which is obtained from $C_4$ cuts which originate from steamcrackers and from which butadiene and isobutene have already been removed. For instance, typical raffinate II contains around 50% by weight of 1-butene.

It can be shown that a high proportion of 1-butene in the hydrocarbon mixture provided has a favorable effect on the linearity of the oligomerizate. It is therefore unsurprising that WO99/25668A1, proceeding from the raffinate II raw material, produces $C_8$ product mixtures having an iso index less than 1.

Nierlich too, in his above-cited article "Oligomerize for better gasoline", emphasizes that raffinate II is of better suitability as starting material for an oligomerization than raffinate III. "Raffinate III" is obtained by removing 1-butene from raffinate II, and for that reason has a much lower 1-butene content than raffinate II. Since 1-butene is likewise an important target product in C4 chemistry, which finds use, inter alia, in the preparation of particular polyethylene-based plastics having a low density (linear low-density polyethylene, LLDPE), there is a great industrial interest in the isolation of 1-butene from raffinate II streams. The effect of this is increasingly that increasingly only raffinate III streams are available for other chemical uses, for example oligomerization.

Because of the current shortage of raw materials as well, petrochemically produced raffinate II is no longer available everywhere in large volumes and under favorable conditions. For instance, some of the $C_4$ olefin mixtures obtained from alternative raw material sources contain hardly any 1-butene, but contain predominantly 2-butene.

One particular example here is FCC-$C_4$, which originates from fluid-catalytic crackers. Other low-1-butene $C_4$ sources are chemical processes such as the dehydrogenation of butenes, and the fermentation or pyrolytic conversion of renewable raw materials.

In contrast to conventional crack-$C_4$, these alternative $C_4$ mixtures do not just have a low proportion of 1-butene but are also subject to variations with time in terms of their composition:

Thus, the $C_4$ stream from an inconstant source can generally be regarded as a sum total of individual mass flows of pure substances, with variation in the respective substance mass flow rates within particular ranges of substance mass flow rates with a particular rate of variation. Table 1 shows the dynamic specification of a $C_4$ stream having a composition which varies with time.

TABLE 1

Dynamic specification of an inconstant $C_4$ stream

| Substance | Substance mass flow rate | Rate of variation |
|---|---|---|
| Isobutene: | 0 kg/s to 1 kg/s | $-0.05$ g/s$^2$ to $0.05$ g/s$^2$ |
| 1-butene: | 0 kg/s to 6 kg/s | $-0.30$ g/s$^2$ to $0.30$ g/s$^2$ |
| 2-Butene (cis + trans): | 1 kg/s to 13 kg/s | $-0.30$ g/s$^2$ to $0.30$ g/s$^2$ |
| Isobutane: | 0 kg/s to 3 kg/s | $-0.15$ g/s$^2$ to $0.15$ g/s$^2$ |

TABLE 1-continued

Dynamic specification of an inconstant $C_4$ stream

| Substance | Substance mass flow rate | Rate of variation |
|---|---|---|
| n-Butane: | 1 kg/s to 7 kg/s | −0.30 g/s² to 0.30 g/s² |
| Other materials: | 0 kg/s to 1 kg/s | −0.05 g/s² to 0.05 g/s² |

Thus, a stream according to the specification could deliver 1 kg of 1-butene per second, and this value could vary at a rate of 0.25 g/s². This means that, within 100 000 seconds (=28 hours), the component mass flow rate of 1-butene rises up to 3.5 kg/s. Conversely, a decrease in the 1-butene with a rate of variation of −0.1 g/s² is also in accordance with the specification, and so a 1 kg/s 1-butene stream dries up completely within less than 3 hours (namely within 10 000 seconds), and so the $C_4$ stream is suddenly free of 1-butene. Since all the components are subject to variations with time, there may also be variations in the total mass flow rate. These variations are limited by the limits of the operating range of the particular plant.

The preparation of high-quality oxo process alcohols from such inconstant raw material sources is the technically demanding background to this invention. In spite of the technical difficulties, there is great economic interest in such a process, since the increasing scarcity of $C_4$-containing raw material streams means that smaller streams from many different sources will have to be used in combination in the future, in order to be able to adequately supply world-scale plants for $C_4$ processing. These streams therefore have very different compositions, which may even vary according to the time of year in some cases. This leads to a much more inconstant raw material supply than supply with crack-$C_4$ from one or few naphtha crackers which has been customary to date.

Both in the field of oligomerization and in that of hydroformylation, the first attempts have been made to deal with varying reactant quality:

WO 99/25668 A1 states that the skeletal isomerization of the $C_8$ product can be affected by recycling of a portion of the reactor output into the reaction.

German patent application DE 102013212481.3, which was still unpublished at the filing date, shows that it is still possible to produce a product with comparatively good isomer distribution even from inferior low-1-butene $C_4$ streams. Both the literature sources are in agreement that, for the production of a plasticizer that meets user expectations, it is possible to use only dibutene streams having a low level of branching as starting material for the hydroformylation. The level of branching is assessed using the iso index according to formula (1). The lower the iso index, the less branched the structure of the molecules within the mixture. DE 102013212481.3 states that preferably only $C_8$ olefin mixtures having an iso index of less than 1.10 are usable for further processing to give plasticizer alcohols. Particular preference is even given to using only mixtures having an iso index of less than 1.05.

When rhodium complexes are used as catalyst for hydroformylation, the ligand is another crucial factor for the product composition of the aldehydes. Unmodified rhodium-carbonyl complexes catalyze the hydroformylation of olefins having terminal and internal double bonds, where the olefins may also be branched, to give aldehydes having a high level of branching. The proportion of terminally hydroformylated olefin is usually lower compared to the cobalt-catalyzed product.

A ligand-modified catalyst system consisting of rhodium and triorganophosphine, e.g. triphenylphosphine, hydroformylates only olefins having a terminal double bond with high selectivity. There is barely any occurrence of isomerization of the double bond and hydroformylation of the internal double bonds.

The hydroformylation of olefins having internal double bonds over catalyst systems containing sterically demanding bisphosphite ligands, in the case of long-chain olefins, proceeds with good selectivity but not with satisfactory activity. In this regard, see:

P. W. N. M. van Leeuwen, in Rhodium Catalyzed Hydroformylation, P. W. N. M. van Leeuwen, C. Claver (eds.), Kluwer, Dordrecht, 2000.

Rhodium-monophosphite complexes in catalytically active compositions, in contrast, are suitable for the hydroformylation of branched long-chain olefins having internal double bonds.

Since the 1970s, there have been descriptions of the use of "bulky phosphites" in hydroformylation:

H. Tricas, O. Diebolt, P. W. N. M. van Leeuwen, Journal of Catalysis, 2013 (298), p. 198-205

These feature good activity, but the n/i selectivity for terminally hydroformylated compounds is in need of improvement.

As well as the use of pure ligands, the use of ligand mixtures has also been described in the literature.

US 20120253080 describes the use of monophosphites with bisphosphites. They are used as a "monitoring ligand". Bisphosphites have much higher complex formation constant than monophosphites and thus form more stable but less active catalyst complexes. However, this combination has the disadvantage that, although the bisphosphites have excellent selectivity, their activity in the case of long-chain olefins is in need of improvement, since not only the selectivity for the desired product but also the space-time yield and the activity of the catalyst system play a crucial role in an industrial scale process. Moreover, the bisphosphites are usually much more costly to prepare than, for example, monophosphites.

EP1099678B1 describes the combined use of phosphonites with bisphosphites. However, it is disadvantageous here is that both ligand types are very costly to produce, and an industrial scale process can therefore hardly be economically viable. Moreover, the addition of the bisphosphite ligand noticeably affects the yield of the reaction, since these ligands are less active when dibutene, for example, is used as substrate. A further problem is that phosphonites are also very much less stable than other organophosphorus ligands.

According to the process chosen, the discharge from the dibutene hydroformylation contains a mixture of the isomeric $C_9$ aldehydes (called isononyl aldehydes, INAL for short) and the isomeric C9 alcohols (called isononyl alcohols, INA for short). The mixture arises from the fact that hydroformylation catalysts are also hydrogenation-active to a certain degree, meaning that they catalyze the reaction of the aldehydes with the hydrogen present in the synthesis gas to give alcohols. Since only the isononyl alcohols are used for the envisaged application, the discharge from the hydroformylation is subjected to a hydrogenation in order to convert the aldehydes present to alcohols. The catalytic hydrogenation of aldehydes to alcohols has been broadly described in the literature; it may proceed either with heterogeneous catalysis or with homogeneous catalysis. An overview is given by J. Falbe, H. Bahrmann, W. Lipps, D. Mayer, G. D. Frey, Alcohols Aliphatic in Ullmann's Encyclopedia of Industrial Chemistry, 2013
and
D. Sanfilippo, P. N. Rylander, Hydrogenation and Dehydrogenation in Ullmann's Encyclopedia of Industrial Chemistry, 2009.

The hydrogenation process does not have any measurable influence on the isomer distribution, meaning that the skeletal isomers of the aldehyde are found in the same ratio in the alcohol.

EP1430014B1 discloses that the isomer distribution of the isononyl alcohol directly affects the properties of the plasticizer produced therefrom by esterification. Esterification with carboxylic acids, especially with phthalic acid, is likewise well-known. In industry, the alcohol mixture is esterified with phthalic acid or phthalic anhydride. The product used as plasticizer is then the diisononyl phthalate (DINP). This can in principle also be prepared by transesterification of a dialkyl phthalate with isononyl alcohol; in this context, dimethyl phthalate in particular is used. EP1430014B1 shows that the process step of esterification has no influence on the quality of the plasticizer; this is determined exclusively by the properties of the $C_9$ alcohol.

There are qualitative rules for the dependence of the performance properties on the structure. Wilson, for example, discusses the properties of phthalates as a function of the total carbon number, meaning the molar mass, and the level of branching, i.e. the isomer composition among other factors:

Alan S. Wilson, Plasticizers, The Institute of Materials, 1995, ISBN 0 901716 76 6, pages 135-136.

Given the same molar mass, for example, the effects of increasing branching include the adverse effects of increasing viscosity, rising vapor pressure, which is associated with a higher volatility, lower plasticizing action and lower thermal and light stability.

Conversely, high branching also brings about positive effects, namely better PVC compatibility, lower migration, greater hydrolysis resistance, lower biodegradation (during the use phase) and higher electrical resistance.

It is immediately apparent that there is no best plasticizer; a compromise has to be made according to the use. Thus, if the plasticizing effect is the most important, a plasticizer having minimum branching will be preferable. If, in contrast, the aim is to produce cable sheathing with PVC, products having somewhat higher branching if anything will be chosen because the electrical insulating action is better.

Using some synthetically prepared individual isomers of DINP, Wadey et al. show very clearly how important properties depend on the structure of the esters:

Brian L. Wadey, Lucien Thil, Mo A. Khuddus, Hans Reich; The Nonyl Phthalate Ester and Its Use in flexible PVC, Journal of Vinyl Technology, 1990, 12, p. 208-211

In summary, it can be stated that the performance properties depend on the structure of the phthalate, the latter depends fundamentally on the structure of the alcohol, and the latter in turn depends considerably on the structure of the parent olefin. An additional complicating factor is that these compounds are produced as isomer mixtures.

Once a formulation has been developed, it then has to be ensured in production that a product having uniform properties is produced. For example, in the case of lubricants, viscosity can vary only within tight limits, in order to comply with the desired viscosity class. In the case of plasticizers, for example, the plasticizing action must remain constant, in order not to force the processors of the plasticizer into constant formulation adjustment, or the electrical resistance must not be below a limit. Constant production monitoring through performance tests is, however, completely impossible for reasons of time, quite apart from the costs that this would cause.

Keeping the isomer composition of the input mixture constant could theoretically solve the problem, but this cannot be sustained in practice. A cracker is operated not in order to give a $C_4$ stream of constant composition, but in order to produce ethylene, propylene, gasoline or other mass products. In practice, the composition of the $C_4$ stream available from the cracker will always vary according to the composition of its raw material and according to the mode of operation. The problem becomes more serious when $C_4$ streams are bought in from different crackers, as is nowadays common practice in large-scale production and will ever more frequently be the case in the future.

Merely by virtue of the raw material at the start, there will therefore inevitably be changes in the composition of the product, and hence changes in the isomer distribution and therefore changes in the performance properties. As already discussed above, further changes in the product composition come to rise in the downstream steps of oligomerization and hydroformylation, for example through alteration of the operating conditions or ageing of the oligomerization catalyst.

According to all of the above, it can be stated that the problem of constant product quality has to date not been highlighted in a holistic manner. The individual process steps have always been considered as independent units. The quality of the plasticizer produced by conventional processes varies within defined limits, this variation being random and dependent on numerous outside influences.

SUMMARY OF THE INVENTION

One problem underlying the invention is that of specifying a process for producing oxo process alcohols from varying raw material sources, which allows production of a constant plasticizer quality over a long production period. In addition, the process should take account of market demand and, if required, enable a higher throughput while maintaining product quality.

In one embodiment, these problems are solved
  by control of the temperature and/or the conversion of the oligomerization as a function of the current composition of the oligomerizate;
  and by control of the composition of the catalyst system and/or of the pressure of the hydroformylation as a function of the current composition of the aldehydes.

In one embodiment, it is one requirement of the two control regimes that the composition of the oligomerizate and the composition of the aldehydes are determined.

These measures are applied to a conventional process for continuously preparing an alcohol mixture of the type specified at the outset.

In one embodiment, the present invention relates to a process for continuously preparing an alcohol mixture, said process comprising:
  oligomerizing an input mixture, which comprises an olefin and has a composition that changes over time, to obtain an oligomerizate comprising olefin oligomers;
  hydroformylating at least a portion of the olefin oligomers present in the oligomerizate with carbon monoxide and hydrogen in the presence of a homogeneous catalyst system to give aldehydes; and subsequently hydrogenating at least a portion of the aldehydes to obtain said alcohol mixture;

wherein a composition of the oligomerizate and a composition of the aldehydes are determined during said process, a temperature and/or a conversion in the oligomerization are controlled as a function of a current composition of the oligomerizate, and a composition of the catalyst system and/or a pressure during the hydroformylating are controlled as a function of a current composition of the aldehydes.

In another embodiment, the present invention relates to an alcohol mixture, prepared by the above process.

In yet another embodiment, the present invention relates to a process for preparing an ester mixture, comprising:

esterifying the above alcohol mixture with an acid, to obtain said ester mixture.

In yet another embodiment, the present invention relates to an ester mixture, prepared by the above process for esterification.

In another embodiment, the present invention relates to a polyvinyl chloride, comprising the above ester mixture.

LIST OF REFERENCE NUMERALS

Figure 1:
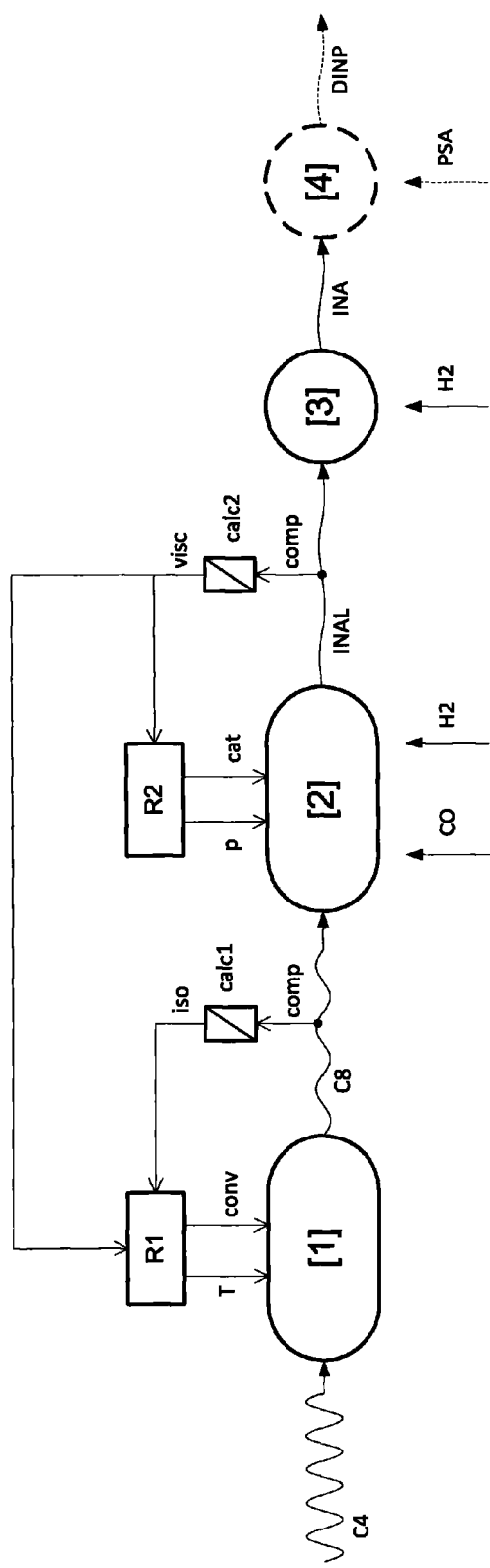
FIG. 1 shows a schematic diagram of a production line for performance of a process according to the invention.

C4 feedstock mixture
[1] oligomerization
C8 dibutene
[2] hydroformylation
CO carbon monoxide
H2 hydrogen
INAL aldehyde mixture
[3] hydrogenation
INA alcohol mixture (INA)
[4] esterification
PSA phthalic anhydride
DINP ester mixture (diisononyl phthalate)
comp analysis of the composition
R1 closed-loop controller for the oligomerization
calc1 computer for determination of the iso index
iso iso index of the dibutene
T temperature for the oligomerization
cony conversion of the oligomerization
R2 closed-loop controller for the hydroformylation
calc2 computer for determination of the viscosity
vise approximate viscosity of the DINP
p pressure in the hydroformylation
cat catalyst composition in the hydroformylation.

DETAILED DESCRIPTION OF THE INVENTION

The invention provides a process for continuously preparing an alcohol mixture, in which an input mixture which comprises olefins and has a composition that changes over time is subjected to an oligomerization to obtain an oligomerizate and at least a portion of the olefin oligomers present in the oligomerizate are hydroformylated with carbon monoxide and hydrogen in a hydroformylation in the presence of a homogeneous catalyst system to give aldehydes, at least some of which are converted to the alcohol mixture by subsequent hydrogenation, in which the composition of the oligomerizate and the composition of the aldehydes are determined, in which the temperature and/or the conversion of the oligomerization are controlled as a function of the current composition of the oligomerizate, and in which the composition of the catalyst system and/or the pressure in the hydroformylation are controlled as a function of the current composition of the aldehydes.

A basic concept of the present invention, both in the oligomerization and in the hydroformylation, is to control the variations in the feedstocks in a compensating manner while taking account of existing feedback effects. Therefore, a systemic control approach is pursued, which covers the two reactions that are crucial for the product quality of the oxo process alcohols and the plasticizers produced therefrom.

Since the inventive control regime takes account of feedback, this is in fact more of a regulation regime (closed-loop control regime) than a control regime in the narrower sense of German terminology. However, since not every terminology system differentiates between the terms "control" and "regulation", the term "control" is used here in order to avoid translation problems.

In order to enable the control of the individual process steps of "oligomerization" and "hydroformylation", the overall process is described by means of a few meaningful parameters. Indicators used are the composition of the oligomerizate and the composition of the aldehydes drawn off from the hydroformylation.

On the basis of these two parameters, the component processes of oligomerization and hydroformylation can be controlled such that either variations in the raw material quality and/or the ageing of catalysts can be compensated for, or such that, if required, a higher production volume can be achieved with the same raw material input.

According to the invention, the two reactions are controlled not just via the standard process parameters of pressure and temperature but, in the case of the oligomerization, also via the conversion of the reaction and, in the case of hydroformylation, additionally via the composition of the catalyst system. The process according to the invention makes use of manipulated variables which have not been utilized in this way to date.

Conversion in the oligomerization is understood to mean the percentage by mass of the olefins introduced into the oligomerization that are converted to olefin oligomers. The conversion can be influenced by the pressure, temperature, residence time and specific catalyst loading. Preferably, the conversion in the oligomerization is controlled via the product recycling. More of that later.

Variation in the composition of the catalyst system in the hydroformylation is understood to mean that the homogeneous catalyst system utilized is not the same throughout; instead, the physical composition of the catalyst system is varied. Specifically, this means that the mixing ratio of the ligands which add onto the central metal and thus form a catalytically active complex is varied in the course of operation. More of that later as well.

As an industrial process, the inventive preparation of the oxo process alcohols is operated continuously. This means that input mixture is introduced into the process and oxo process alcohols are produced therefrom round the clock every day of the week. Taking account of the standard shutdown and inspection periods, at least 8000 operating hours are expected per year.

With regard to the continuous mode of operation, the measurements of the composition of the oligomerizate and composition of the aldehydes should likewise be determined continuously, such that the oligomerization and/or the hydroformylation can also be controlled continuously. The frequency of the measurements is chosen as a function of the rate of variation of the input mixture. Initial experience from operation shows that a measurement of the compositions every couple of hours is sufficient, especially since the controlled chemical reactions do not react instantaneously to the variation in their manipulated variables. If, as in the above-described scenario, a total loss of the 1-butene within fewer than 3 hours were to be expected, shorter measuring intervals would of course be required. If the variations are more moderate, it may also be sufficient to conduct the measurements every 12 or 24 hours. A "continuous determination" in this context is thus understood to mean an adjustment of the measurement intervals to the expected rate of variation of the particular parameter. Where reference is made to a current composition, this means the composition analyzed at the start of the current measurement interval.

The manipulated variables can in principle be controlled manually with regard to the measurements from the analysis by the personnel running the production plant. In the interests of a high level of automation, however, the control regime is implemented in a process control technique known per se.

The analysis of the composition of the aldehydes results in a multidimensional data set. This makes the control of the hydroformylation very complex. It is therefore easier and hence more effective to control the oxo process reaction, by firstly using the composition of the aldehydes to calculate a scalar controlled variable, and setting up the control regime so as to keep this controlled variable constant. According to this concept, a one-dimensional (scalar) parameter is thus calculated by a fixed mathematical calculation method from the multidimensional data set which reflects the composition of the aldehydes drawn off from the hydroformylation. This then serves as the controlled variable, which is kept constant by adjusting the pressure and/or the catalyst composition of the hydroformylation as soon as the controlled variable deviates from a given target value. The pressure and/or catalyst composition is then controlled by a conventional closed-loop controller with proportional, integral, differential or PID characteristics.

Incidentally, keeping a parameter constant in this context is not necessarily understood to mean that it is mathematically constant, but rather that the closed-loop control of the controlled variable allows certain deviations from the target quantity, with suitable setting of the tolerance of the closed-loop controller. A constant controlled value is thus understood to mean compliance with a tolerance value range around the actual target quantity (constant for closed-loop control purposes).

Appropriately, it is not just the hydroformylation but also the oligomerization that is controlled in this way. Accordingly, the temperature and/or conversion in the oligomerization is/are likewise controlled such that the first scalar controlled variable calculated from the composition of the aldehydes is kept constant. Closed-loop control can be effected here too with P, I, D or PID characteristics.

The combined control of oligomerization and hydroformylation with regard to keeping constant the first scalar controlled variable that represents the aldehyde composition improves the control quality of the overall process and hence makes the product quality of the oxo process alcohols produced more constant.

Especially when the oxo process alcohols produced are intended for further processing to give plasticizers, it is advantageous when the first scalar controlled variable used is an approximation of the viscosity of the ester mixture obtainable by esterification of the alcohol mixture or by transesterification with the aid of the alcohol mixture.

Oxo process alcohols are only of limited usability as plasticizers for plastics. PVC in particular can be plasticized better with an ester mixture which is prepared from the oxo process alcohol. This is accomplished either by reaction of the alcohol with an acid (esterification) or by transesterification of an existing ester in the presence of the alcohol. The viscosity of the ester mixture is crucial to the product quality of the plasticizer produced. It has been found that the viscosity of the plasticizer formed from the composition of the aldehydes can be predicted in a good approximation since neither the hydrogenation of the aldehydes to the alcohols nor the conversion thereof to the target esters has any influence on the viscosity thereof.

It is admittedly known from EP1430014B1 that, for example, the viscosity η of a phthalic ester mixture obtainable by esterifying phthalic acid or phthalic anhydride with a mixture of isomeric alkyl alcohols can be calculated in a good approximation by the formula (2):

$$\ln(\eta) = \Sigma x_i \ln(\eta_i) \qquad (2)$$

where $x_i$ is the mole fraction of the isomerically pure alcohol and $\eta_i$ is the viscosity index of the isomerically pure alcohol.

According to the invention, however, the approximation of the viscosity η of the ester mixture which is used as the first scalar control variable is calculated not from the alcohols but actually from the aldehydes. For this purpose, formula (2) is likewise used, but in that case $x_i$ is the mole fraction of the particular isomerically pure aldehyde and $\eta_i$ is the contribution of the isomerically pure aldehyde to the viscosity.

The advantage of calculating the approximate viscosity from the aldehydes rather than from the alcohols is that the parameter to be controlled is determined immediately downstream of the process to be controlled, and not with a further time delay downstream of the hydrogenation. Therefore, the response behavior of the closed-loop control circuit is much better.

The parameters $x_i$ required for the calculation of the first scalar controlled variable η in formula (2), i.e. the mole fractions of the individual isomeric aldehydes of the aldehyde mixture, are obtained by the analysis of the composition of the aldehyde mixture. This can be accomplished by gas chromatography in a known manner. The coefficients likewise required $\eta_i$ represent the contributions of the particular isomeric aldehyde to the viscosity and are therefore natural constants. They are determined experimentally once for the aldehydes that occur in the process. The viscosity contributions $\eta_i$ of the aldehydes that are to be expected in the hydroformylation of dibutene are shown in Table 2.

TABLE 2

Viscosity contributions of isomerically pure $C_9$ aldehydes

| Isononyl isomers | Viscosity contribution $\Box_i\Box$ of the isomers | Isononyl isomers | Viscosity contribution $\Box_i\Box$ of the isomers |
|---|---|---|---|
| n-Nonanal | 45.5 | 2,5-Dimethyl-heptanal | 120.2 |
| 2-Methyloctanal | 72.2 | | |
| 2-Ethylheptanal | 98.7 | 6-Methyloctanal | 61.1 |
| 2-Propylhexanal | 98.7 | 4,5-Dimethyl-heptanal | 94.4 |
| 4-Methyloctanal | 67.2 | | |
| 2,3-Dimethylheptanal | 108.4 | 2,3,4-Trimethyl-hexanal | 574.3 |
| 3-Ethylheptanal | 50.5 | 3-Ethyl-4-methyl-hexanal | 120.6 |
| 2-Propyl-3-methyl-pentanal | 229.5 | | |
| 2-Ethyl-4-methylhexanal | 158.4 | 3,5,5-Trimethyl-hexanal | 111.8 |
| | | Remainder | (173.1) |

The viscosity is highly dependent on the measurement temperature and also on the measurement method. The rule for the individual viscosity contributions $\eta_i$, like the overall viscosity of the ester mixture, is that they are reported under standard conditions (293.15 K and 1013 mbar absolute).

A multidimensional measurement is also obtained for the control of the oligomerization, namely the composition of the oligomerizate. Here too, it is opportune in the interests of the effectiveness of the closed-loop control to convert this multidimensional measurement to a second scalar controlled variable and likewise to keep it constant, as described above analogously for the hydroformylation.

The second scalar controlled variable employed, which is required for the control of the oligomerization, is preferably an approximation of the iso index of the olefin oligomers. The iso index is a measure of the level of branching of the oligomerizate. In the case of dibutene, it states the mean number of methyl groups per $C_8$ molecule in the isomer mixture. The iso index for dibutene is defined according to formula (1).

The calculation of the iso index as the second scalar controlled variable requires merely the proportion by weight of the methylheptenes and the proportion by weight of the dimethylhexenes in the oligomerizate. These can be determined in a known manner, for example, by hydrogenating gas chromatography.

If the hydroformylation is supplied not with the entire oligomerizate but only with a portion of the olefin oligomers formed, it is preferable to determine only the iso index of the olefin oligomers to be hydroformylated.

In principle, the measures described here can be applied to any process for preparing oxo alcohols from olefins which proceeds via the route of oligomerization, hydroformylation, hydrogenation. The number of carbon atoms in the olefins used and the resulting number of carbon atoms in the oxo process alcohols are immaterial. It is possible to use input mixtures based on ethene, propene, butene or pentene, and to produce the oxo process alcohols having 3, 5, 7, 9, 11 and 13 carbon atoms.

The examples are concerned with a $C_4$-based process for preparing INA. However, the person skilled in the art will be able to apply the findings demonstrated directly to $C_2$-, $C_3$- or $C_5$-based processes.

In the case of use of butene as raw material, it should be noted that the oligomerization forms not only the desired $C_8$ olefins but also those having twelve, sixteen or more carbon atoms. For preparation of isononanol, it is therefore necessary to separate the dibutenes from the oligomerizate. Thus, in a development of the invention, the input mixture used comprises olefins having four carbon atoms which are oligomerized in the course of the oligomerization to give olefin oligomers having eight, twelve and sixteen carbon atoms, and the olefin oligomers having eight carbon atoms are removed from the oligomerizate and hydroformylated to aldehydes having nine carbon atoms.

The process according to the invention is of excellent suitability for producing oxo process alcohols of constant quality from varying raw material streams. If a $C_4$-based process is being operated, it is entirely possible to process input mixtures having the specification according to Table 1.

Such a highly variable $C_4$ stream may originate from different sources and in particular from inexpensive sources. It is also possible to use a $C_4$ cut combined from different sources.

The oligomerization is effected in a known and proven manner over a heterogeneous nickel catalyst. In this respect, reference is made to the literature relating to the OCTOL process.

The oligomerization can be conducted in a plurality of stages.

The oligomerization is preferably operated in circulation mode, in such a way that a portion of the unconverted butenes present in the oligomerizate drawn off from the oligomerization is recycled into the oligomerization. This is because circulation mode opens up the option of controlling the conversion in the oligomerization by varying the proportion of the butenes recycled. The controllability of the conversion via the proportion of the butenes recycled is described in detail in WO 99/25668 A1, and in the German patent application DE 102013212481.3 which was still unpublished at the filing date.

The composition of the homogeneous catalyst system in the hydroformylation is controlled by using a catalyst system comprising rhodium and potentially at least two different monophosphite ligands, the mixing ratio of which is actively influenced by metering in one of the two monophosphite ligands. If one of the two ligands is metered in, there is a shift in the mixing ratio in its favor. At the limits of the mixing range, it may be the case that one ligand is present only in traces in the system.

The wording that the catalyst system "potentially" comprises ligands should be understood here such that the ligands in question are present in the reaction mixture and hence are available in principle for formation of the catalyst system. However, this does not mean that all the ligands present in the reaction system are catalytically active: this is because, in practice, an excess of ligand is always supplied to the reaction system, and so it is not possible for the full amount of ligand to complex to rhodium and therefore be catalytically active. Ultimately, it is not possible to say exactly which ligand is complexed and hence becomes catalytically active. In the context of the invention, however, it is crucial to give the ligands added the possibility in principle of becoming an active part of the catalyst system. Any substance present in the reaction mixture which is capable of forming a catalytically active complex with rhodium is therefore referred to as a potential ligand.

The shift in the mixing ratio of the ligands that are potentially active in the catalyst complex is accomplished in such a way that the molar ratio of the sum total of all the monophosphite ligands to rhodium remains constant, taking account of ligand losses, and within the technical possibilities and measurement accuracies. The reason for this proviso is that ligand is lost with time in every Rh-catalyzed hydroformylation, whether through deactivation, breakdown or loss via the product discharge. In order keep the concentration of the active catalyst system in the reaction mixture constant, it is thus necessary to continue to constantly meter in ligand. A preferred development of the invention thus envisages, when using a catalyst system having a plurality of ligands, not always continuing to meter in all the ligands in the same (original) mixing ratio, but continuing to meter in one of the ligands preferentially in order to influence the composition of the catalyst system and hence the overall hydroformylation in a controlled manner. In that case, the loss of one ligand is compensated to a lesser degree than that of the other.

Preference is given to using a catalyst system potentially comprising exactly two ligands. In this case, a first ligand is used as "base ligand", which is present in a high concentration and accomplishes the catalysis to a crucial degree. The base ligand used is, for example, an inexpensive monophosphite. Meanwhile, the second ligand is used as "control ligand" in order to control the selectivity of the hydroformylation through metered addition. The control ligand should have a much greater selectivity than the base ligand in order to be able to influence the selectivity of the oxo reaction in a controlled manner. Therefore, the control ligand will be much more expensive than the base ligand, and it is therefore used only in a low concentration in practice compared to the base ligand. Unlike the bisphosphite "monitoring" ligands customary in the related art, the inventive control ligand should have activity at least approximately comparable to the base ligand.

Specifically, one option is to always completely compensate for the expected losses of the base ligand and, as desired, to completely or partially compensate or to overcompensate for the losses of the control ligand, according to the direction in which the selectivity of the hydroformylation is to be controlled.

If a catalyst system having exactly two ligands is utilized, one option as a first monophosphite ligand, i.e. as a base ligand, is a compound according to structural formula II. The second monophosphite ligand (control ligand) chosen may then be a compound according to one of the following structural formulae Ia, Ib and III:

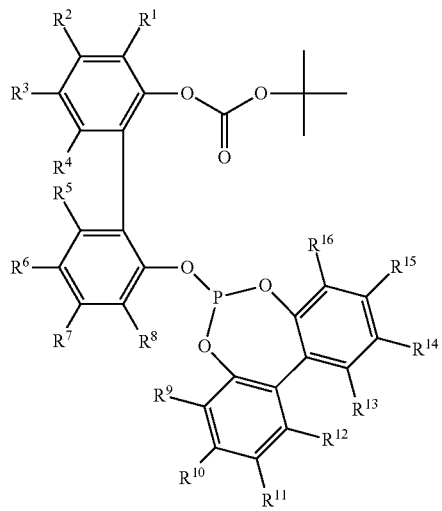

where, in Ia,
$R^1$, $R^2$, $R^3$, $R^4$, $R^5$, $R^6$, $R^7$, $R^8$ are each independently selected from:

—H, —($C_1$-$C_{12}$)-alkyl, —O—($C_1$-$C_{12}$)-alkyl, —O—($C_6$-$C_{20}$)-aryl, —($C_6$-$C_{20}$)-aryl, halogen, COO—($C_1$-$C_{12}$)-alkyl, CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —SO$_3$H, —SO$_3$Na, —NO$_2$, —CN, —NH$_2$, —N[($C_1$-$C_{12}$)-alkyl]$_2$;

where $R^9$, $R^{10}$, $R^{11}$, $R^{12}$, $R^{13}$, $R^{14}$, $R^{15}$, $R^{16}$ are each independently selected from:

—H, —($C_1$-$C_{12}$)-alkyl, —O—($C_1$-$C_{12}$)-alkyl, —O—($C_6$-$C_{20}$)-aryl, —($C_6$-$C_{20}$)-aryl, -halogen, —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —SO$_3$H, —SO$_3$Na, —NO$_2$, —CN, —NH$_2$, —N[($C_1$-$C_{12}$)-alkyl]$_2$;

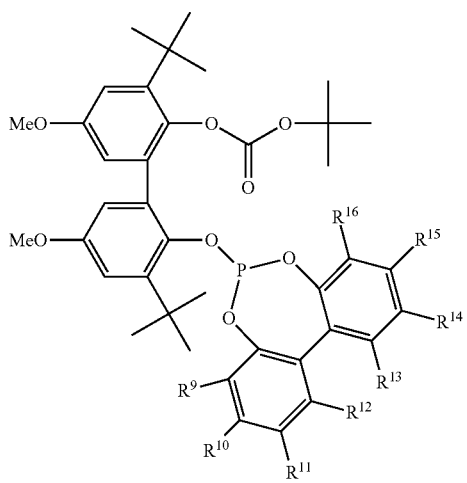

where, in Ib,
$R^9$, $R^{10}$, $R^{11}$, $R^{12}$, $R^{13}$, $R^{14}$, $R^{15}$, $R^{16}$ are each independently selected from:

—H, —($C_1$-$C_{12}$)-alkyl, —O—($C_1$-$C_{12}$)-alkyl, —O—($C_6$-$C_{20}$)-aryl, —($C_6$-$C_{20}$)-aryl, -halogen, —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —SO$_3$H, —SO$_3$Na, —NO$_2$, —CN, —NH$_2$, —N[($C_1$-$C_{12}$)-alkyl]$_2$.

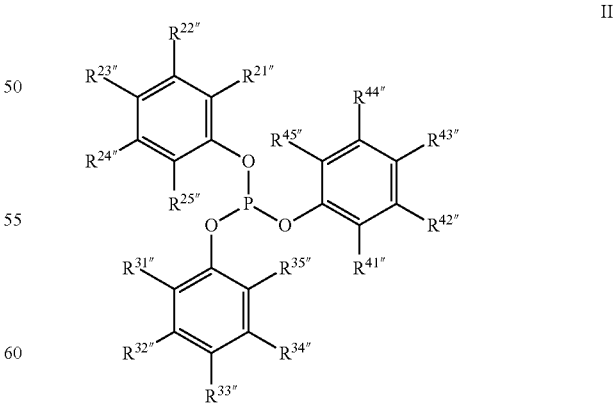

where, in II,
$R^{21''}$, $R^{22''}$, $R^{23''}$, $R^{24''}$, $R^{25''}$, $R^{31''}$, $R^{32''}$, $R^{33''}$, $R^{34''}$, $R^{35''}$, $R^{41''}$, $R^{42''}$, $R^{43''}$, $R^{44''}$, $R^{45''}$ are each independently selected from:

—H, —($C_1$-$C_{12}$)-alkyl, —O—($C_1$-$C_{12}$)-alkyl, —O—($C_6$-$C_{20}$)-aryl, —($C_6$-$C_{20}$)-aryl, -halogen, —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —SO$_3$H, —SO$_3$Na, —NO$_2$, —CN, —NH$_2$, —N[($C_1$-$C_{12}$)-alkyl]$_2$.

Preferably, in II, $R^{21"}$, $R^{22"}$, $R^{23"}$, $R^{24"}$, $R^{25"}$, $R^{31"}$, $R^{32"}$, $R^{33"}$, $R^{34"}$, $R^{35"}$, $R^{41"}$, $R^{42"}$, $R^{43"}$, $R^{44"}$, $R^{45"}$ are each independently selected from:

—H, —O—($C_1$-$C_{12}$)-alkyl, —O—($C_6$-$C_{20}$)-aryl, —($C_6$-$C_{20}$)-aryl.

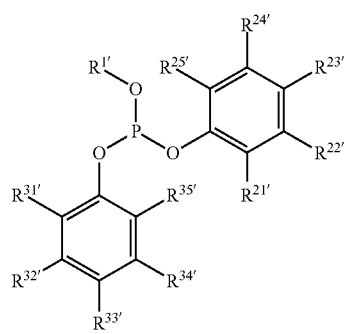

III where, in III, $R^{1'}$ is selected from:

—($C_1$-$C_{12}$)-alkyl, —($C_3$-$C_{12}$)-cycloalkyl, and $R^{21'}$, $R^{22'}$, $R^{23'}$, $R^{24'}$, $R^{25'}$, $R^{31'}$, $R^{32'}$, $R^{33'}$, $R^{34'}$, $R^{35'}$ are each independently selected from:

—H, —($C_1$-$C_{12}$)-alkyl, —O—($C_1$-$C_{12}$)-alkyl, —O—($C_6$-$C_{20}$)-aryl, —($C_6$-$C_{20}$)-aryl, -halogen, —COO—($C_1$-$C_{12}$)-alkyl, —CO—($C_1$-$C_{12}$)-alkyl, —CO—($C_6$-$C_{20}$)-aryl, —COOH, —OH.

Preferably, in III, $R^{21'}$, $R^{22'}$, $R^{23'}$, $R^{24'}$, $R^{25'}$, $R^{31'}$, $R^{32'}$, $R^{33'}$, $R^{35'}$ are each independently selected from:

—H, —($C_1$-$C_{12}$)-alkyl, —O—($C_1$-$C_{12}$)-alkyl, —O—($C_6$-$C_{20}$)-aryl, —($C_6$-$C_{20}$)-aryl.

All the substances that are covered by the structural formulae Ia, Ib, II and III appear to have similar behaviour with respect to the catalytic characteristics thereof, and so they are suitable as ligands in the context of the invention.

Experiments demonstrate that the following combinations of specific substances are of outstanding suitability as ligands for the controllable catalyst system in the hydroformylation:

a) substance L2 as first monophosphite ligand (base ligand) and substance L3 as second monophosphite ligand (control ligand);

b) substance L2 as first monophosphite ligand (base ligand) and substance L1 as second monophosphite ligand (control ligand);

c) substance L2 as first monophosphite ligand (base ligand) and substance L4 as second monophosphite ligand (control ligand);

where L1, L2, L3 and L4 are defined as follows:

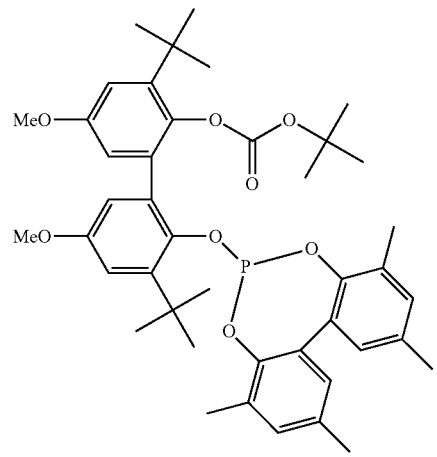

L1

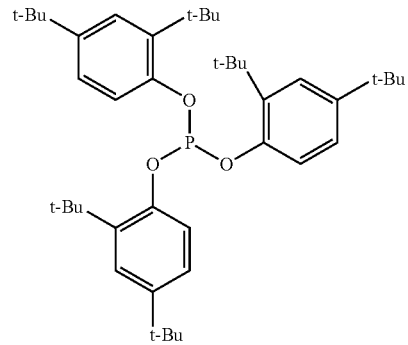

L2

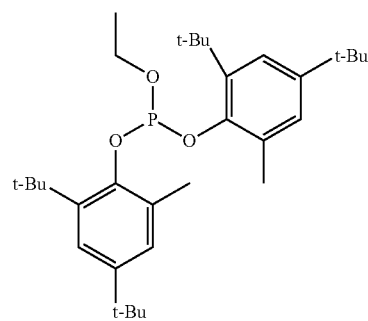

L3

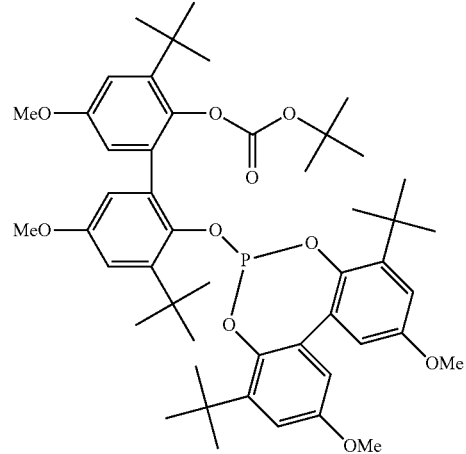

L4

(L2) tris(2,4-di-tert-butylphenyl)phosphite;
(L1) tert-butyl (3,3'-di-tert-butyl-5,5'-dimethoxy-2'-((2,4,8,10-tetramethyldibenzo[d,f][1,3,2]dioxaphosphepin-6-yl)oxy)-[1,1'-biphenyl]-2-yl)carbonate;
(L3) bis(4,6-di-tert-butyl-2-methylphenyl)ethyl phosphite; (L4) tert-butyl (3,3'-di-tert-butyl-2'-((4,8-di-tert-butyl-2,10-dimethoxydibenzo[d,f][1,3,2]dioxaphosphepin-6-yl)oxy)-5,5'-dimethoxy-[1,1'-biphenyl]-2-yl)carbonate.

As the experiments show, the control ligands L1, L3 and L4 are capable of significantly influencing the n/i selectivity which originates from the base ligand L2.

A mixture of base ligand L2 and control ligand L1 or L4 has been found to be of particularly good suitability for control.

The aim of the process according to the invention is the production of oxo process alcohols intended for further processing to give plasticizer esters. Since the quality of these end products depends to a high degree on the quality of the oxo process alcohols, the manufacturers of plasticizers are profiting significantly from the benefits of this process.

Protection is consequently also sought for a process for producing an ester mixture, especially for use thereof as a plasticizer for polyvinyl chloride (PVC), in which an alcohol mixture produced in accordance with the invention is used.

The basic process procedure and the closed-loop control thereof are now illustrated in detail by FIG. 1. The FIGURE shows:

FIG. 1: Simplified schematic diagram of a production line for performance of a process according to the invention, taking particular account of the streams and closed-loop control circuits.

From the left-hand side, an input mixture C4 is supplied from an inconstant source which is not shown. It contains essentially hydrocarbons having four carbon atoms, namely saturated butanes and unsaturated butenes. The composition of the input mixture C4 varies significantly, for instance as recorded in Table 1.

In an oligomerization [1], the butenes are oligomerized, so as to form essentially $C_8$, $C_{12}$ and $C_{16}$ olefins therefrom. The dibutenes $C_8$ are separated from this oligomerizate (not shown) and run into a hydroformylation [2].

The dibutene $C_8$ is hydroformylated therein with carbon monoxide CO and hydrogen $H_2$ to give a mixture of aldehydes having nine carbon atoms INAL.

The aldehydes INAL are subsequently hydrogenated in a hydrogenation [3] with hydrogen $H_2$ to give the corresponding alcohols INA.

In practice, part of the hydrogenation already proceeds as a further reaction in the hydroformylation reactor, since the aldehydes freshly formed in the hydroformylation [2] react further straight away with the hydrocarbon $H_2$ present to give the corresponding alcohols. The fact that the aldehyde mixture INAL drawn off from the hydroformylation [2] already contains some INA, however, is unimportant for the control of the process.

The INA is subsequently reacted in an esterification [4] with phthalic acid or phthalic anhydride PSA to give the ester mixture diisononyl phthalate DINP, which is used as plasticizer for polyvinyl chloride. The esterification [4] is effected in a batch process and is not part of the continuous process for preparing the oxo process alcohols.

In order to compensate for the varying composition of the input mixture $C_4$ and to arrive at an alcohol mixture INA having a less variable product quality, control of the production process is envisaged in accordance with the invention. The particular aim is to produce an ester mixture DINP having a viscosity which varies within a narrow specification window. Since the viscosity of the ester mixture DINP is determined by the viscosity of the aldehyde mixture INAL, the aim of the closed-loop control concept is to keep the viscosity of the aldehydes INAL very substantially constant at a given value.

For this purpose, one closed-loop controller R1 and R2 each is provided for the oligomerization [1] and for the hydroformylation [2].

For the closed-loop control R2 of the hydroformylation [2], the composition comp of the aldehyde mixture INAL is analysed continuously. This is accomplished by gas chromatography. The gas chromatograph passes the mole fractions of the individual isomeric aldehydes in the INAL to a computer calc2, which uses them to calculate, with the aid of the formula (2) and the viscosity contributions recorded in the computer, a first scalar controlled variable visc, which corresponds to an approximation of the viscosity of the ester mixture DINP under standard conditions. If it is possible to keep visc constant within a defined range of values, the ester mixture DINP will also have a virtually constant viscosity. The target value is fixed on the basis of the viscosity specification of the desired DINP plasticizer product. This value is preset as a target value in the closed-loop controller R2. It should be noted that the target value, to be precise, is a target range within which the viscosity may vary without any need for intervention. This target range may, for example, be 90 to 95 mPas, but may also take on completely different values depending on the customer demands on the plasticizer product.

If the actual value of the first scalar controlled variable visc deviates from the target value or leaves the target range, closed-loop controller R2 intervenes in the hydroformylation [2], in order to restore the target viscosity or to guide the viscosity back into the specification range.

The intervention is made via alteration of the pressure p in the hydroformylation [2], or via variation of the catalyst system cat in the hydroformylation [2], or via both measures at the same time.

The pressure in the hydroformylation is exerted via the synthesis gas. The pressure control regime is therefore a closed-loop control regime using the pressure of the synthesis gas.

If the viscosity rises above the target value, it is possible to counteract this by closed-loop control, by lowering the synthesis gas pressure and/or metering in control ligand.

The adjustment of the controlled variable depends on the control ligand used. For the possible control ligand tert-butyl (3,3'-di-tert-butyl-5,5'-dimethoxy-2'-((2,4,8,10-tetramethyldibenzo[d,f][1,3,2]dioxaphosphepin-6-yl)oxy)-[1,1'-biphenyl]-2-yl)carbonate (L1) in mixtures with base ligand tris(2,4-di-tert-butylphenyl)phosphite (L2), experimentally determined dependences were ascertained and shown in Example 1.

For illustration, the closed-loop control parameters determined by way of example are taken as given:

When these two potential ligands are used, an increase in the proportion of control ligand L1 by 10 percentage points leads to an increase in the calculated viscosity by 0.87 mPas with constant feedstock and constant reaction conditions in the hydroformylation.

The dependence of the viscosity parameter visc on the mixing ratio of the ligands used has to be determined experimentally once for each ligand mixture.

Thus, in Example 2, an analogous derivation for the use of a mixture of bis(4,6-di-tert-butyl-2-methylphenyl)ethyl phosphite (L3) and L2 is disclosed. In that case, the proportion of L3 in the mixture has to be raised, for example, by about 20 percentage points in order to achieve an increase in the calculated viscosity by 1 mPas. The values apply correspondingly if the viscosity should fall below the target value.

According to the invention, the closed-loop control of the hydroformylation can also be effected via the (absolute) reaction pressure. Example 3 discloses how the dependence of the controlled variable visc on the pressure can be derived.

Here too, it should be taken into account that the pressure dependence can also depend on the catalyst system (or ligand system) used, for which reason it has to be determined experimentally once in the specific individual case. For the ligand L1, it is apparent that an increase in the pressure by about 6 bar increases the controlled variable visc by 0.5 mPas. The situation is analogous if it is lowered.

As a result of the engineering of the plants, there is of course a limit to the possible variation of pressure, and for that reason the control is preferably effected via the ligand mixture.

The control of the hydroformylation system is illustrated in Example 4.

The closed-loop control of the amount of control ligand metered in and of the change in pressure is effected with PID characteristics.

The oligomerization [1] is controlled via a closed-loop controller R1 likewise having PID characteristics. This serves to keep constant a second scalar controlled variable iso within a preset target range.

The second scalar controlled variable iso is the iso index of the dibutene $C_8$ separated from the oligomerizate, multiplied by 100. The factor of 100 has no effect on the closed loop control system, but merely facilitates read-off and adjustment. To determine the iso index, the dibutene $C_8$ is analysed continuously by means of hydrogenating gas chromatography for its composition. The proportion by weight of the methylheptenes and the proportion by weight of the dimethylhexenes are used by a computer calc1 to calculate, with formula (1), the iso index of the dibutene $C_8$ and, by multiplication of this value by 100, the scalar controlled variable iso.

In order to keep the iso index of the dibutene produced constant within a range optimal for the hydroformylation, closed-loop controller R1 intervenes in the oligomerization [1] by adjusting the temperature T thereof and/or the conversion conv thereof. The reaction temperature T can be raised and lowered by adjusting the cooling water volume of the oligomerization reactor. The temperature T can likewise be raised and lowered by adjusting the temperature of the heat carrier fed in. The conversion conv can be controlled by varying the recycling rate of unconverted butenes into the oligomerization operated in circulation mode.

The determination of the control dependences was likewise conducted experimentally here, and the method is disclosed in Example 5. It becomes clear therein that the dependences between the iso index, conversion and the control parameters of temperature and reflux ratio are somewhat more complex. The dependences derived from the example are reflected in the two formulae (3) and (4):

$$\text{iso} = 113.814 - 0.360474 \cdot T - 4.36236 \cdot R - 0.0618174 \cdot w(1-B) + 0.00518875 \cdot T^2 + 0.0364209 \cdot w^2(1-B) - 0.00545420 \cdot T \cdot w(1-B) + 0.174800 \cdot R^2 \quad (3)$$

$$\text{conv} = -181.465 + 7.52134 \cdot T + 237.263 \cdot R - 1.70002 \cdot w(1-B) - 0.0510611 \cdot T^2 - 4.39695 \cdot T \cdot R + 0.0272597 \cdot T \cdot w(1-B) + 1.08140 \cdot R \cdot w(1-B) \quad (4)$$

where iso and conv are the controlled variables specified in FIG. 1. T represents the temperature (in degrees Celsius) of the heat carrier with which the temperature of the oligomerization reactor is controlled, R indicates the recycle rate of unconverted butenes (in the present experimental examples reported in kg/h) and w(1−B) indicates the proportion by mass of 1-butene in the C4 hydrocarbon stream used.

With the aid of a computer, it is possible to use these dependences to implement a closed-loop control system which reacts to changes in the respective parameters:

If the iso index is too high, in this embodiment of the invention, the temperature of the oligomerization reaction should be lowered. The associated loss of conversion can be compensated for by a suitable increase in the recycle rate.

Meanwhile, if the iso index is sufficiently low that an increase in the temperature is immediately justifiable for the purposes of the specification to be observed, the temperature of the oligomerization can be increased. In general, this results in a rise in the conversion, which is typically also desirable. By reducing the recycling ratio, however, it is also possible to reduce the conversion again in order to prevent unwanted overproduction. One example of such a closed-loop control system is cited in Example 6.

In the embodiment of the invention shown in FIG. 1, closed-loop controller R1, in the setting of temperature and/or conversion in the oligomerization [1], takes account not only of the second scalar controlled variable iso but also of the first scalar controlled variable visc, which is obtained downstream of the hydroformylation [2]:

Since the iso index indirectly has a crucial influence on the viscosity of the plasticizer, the same modes of closed-loop control apply to the control of the viscosity in the reaction system for the oligomerization as to the closed-loop control of the iso index. However, a single experimental determination of the dependences is necessary for the control of the oligomerization by means of the viscosity. For this purpose, the results from Examples 1 and 5 are combined. Here, by way of example, the dependence is shown for a combination of oligomerization and hydroformylation, in which the ligand system for the hydroformylation is formed from L1 and L2:

$$\text{visc} = \{-4.1003453 \cdot \ln [x(L1)] + 65.201179\} \cdot \{[113.814 - 0.360474 \cdot T - 4.36236 \cdot R - 0.0618174 \cdot w(1-B) + 0.00518875 \cdot T^2 + 0.0364209 \cdot w^2(1-B) - 0.00545420 \cdot T \cdot w(1-B) + 0.174800 \cdot R^2]/100\} + \{3.4837009 \cdot \ln [x(L1)] + 21.154949\} \quad (5)$$

where visc is the controlled variable specified in FIG. 1. T represents the temperature (in degrees Celsius) of the heat carrier with which the temperature of the oligomerization reactor is controlled, R indicates the recycle rate of unconverted butenes into the oligomerization (here in kg/h) and w(1−B) indicates the proportion by mass of 1-butene in the C4 hydrocarbon stream used for the oligomerization. Finally, x(L1) represents the molar proportion of the control ligand L1 in the ligand mixture of L1 and L2 (in mol %). In represents the natural logarithm.

If the viscosity of the plasticizer is above target, in the present embodiment of the invention, the temperature of the oligomerization reaction should be lowered. The loss of conversion associated with the lowering of the temperature can be compensated for by a suitable increase in the recycle rate.

Meanwhile, if the viscosity of the plasticizer is sufficiently low that an increase in the temperature is immediately justifiable for the purposes of the specification to be observed, the temperature of the oligomerization can be increased. In general, this results in a rise in the conversion, which is typically also desirable.

One example of the control of the oligomerization with the aid of the controlled variable visc and the joint control of the hydroformylation and oligomerization as an overall process is described as Example 7.

Having generally described this invention, a further understanding can be obtained by reference to certain specific examples which are provided herein for purposes of illustration only, and are not intended to be limiting unless otherwise specified.

EXAMPLES

Procedure for Examples 1 to 3

In a 100 ml autoclave from Parr Instruments, 6 g of the octene mixtures from Table 1 were hydroformylated at 130-140° C., synthesis gas pressure 30 or 50 bar (CO/$H_2$=1:1 (% by vol.)). As catalyst precursor, 0.005 g of Rh(acac)(CO)$_2$ was initially charged for a catalyst concentration of 40 ppm of Rh based on the overall reaction mixture, and correspondingly 0.0123 g of Rh(acac)(CO)$_2$ for a concentration of 100 ppm of Rh. The solvent used was 40 to 46 g of toluene in each case. The ligand L1 or the ligand L2 or the ligand L3 or the ligand L4 or the ligand mixture consisting of ligands L1 and L2 or of ligands L2 and L3 or of ligands L2 and L4 was used in a 20-fold molar excess relative to rhodium (ratio of total phosphorus to rhodium). In addition, as GC standard, about 0.5 g of tetraisopropylbenzene (TIPB) was added. About 6 g of reactant were metered in after the reaction temperature envisaged had been attained.

During the reaction, the pressure was kept constant via synthesis gas regulation with a mass flow meter. The stirrer speed was 1200 min$^{-1}$. Samples were taken from the reaction mixture after 180 minutes.

In the catalysis experiments, the abbreviations L1 to L4 are used for the ligands.

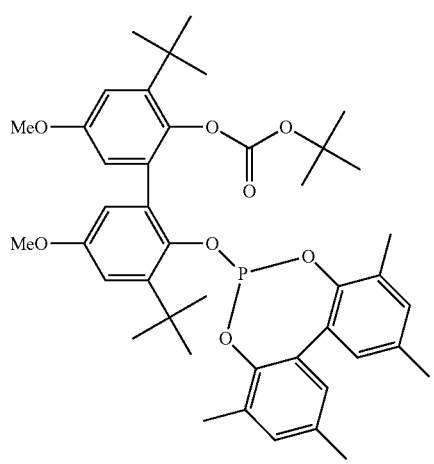

L1

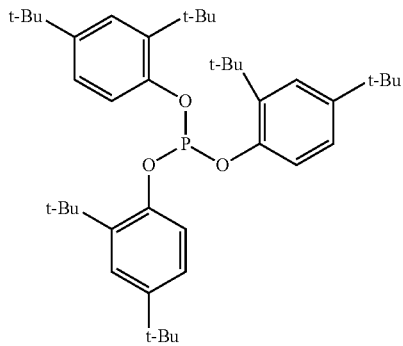

L2

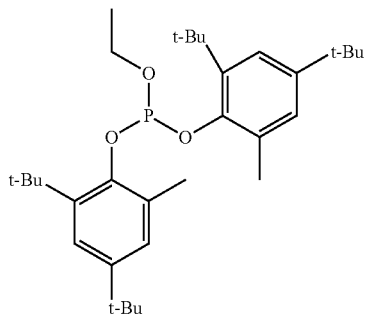

L3

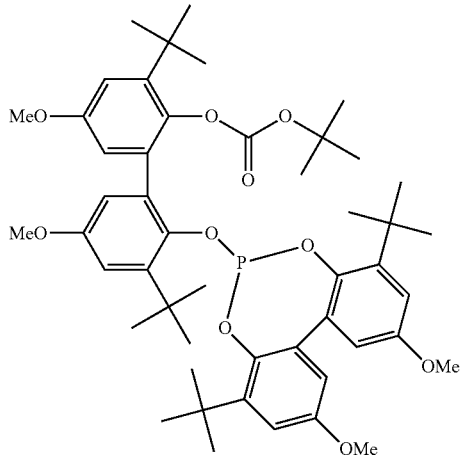

L4

The preparation of the ligands L1, L3 and L4 is described in the experimental section which follows. Ligand L2 (TDT-BPP or Alkanox 240) is commercially available.

General Procedure for Preparation of the Ligands

All the preparations which follow were carried out under protective gas using standard Schlenk techniques. The solvents were dried over suitable desiccants before use (Purification of Laboratory Chemicals, W. L. F. Armarego, Christina Chai, Butterworth Heinemann (Elsevier), 6th edition, Oxford 2009).

All preparative operations were effected in baked-out vessels. The products were characterized by means of NMR spectroscopy. Chemical shifts (δ) are reported in ppm. The $^{31}$P NMR signals were referenced according to: $SR_{31P}=SR_{1H}*(BF_{31P}/BF_{1H})=SR_{1H}*0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84).

Nuclear resonance spectra were recorded by means of a Bruker Avance 300 or Bruker Avance 400; gas chromatography analysis was effected using an Agilent GC 7890A.

Reaction scheme:

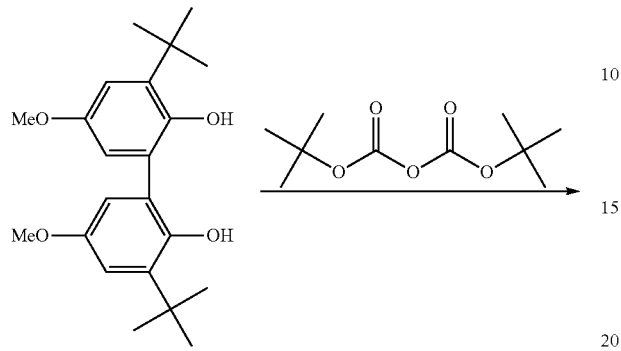

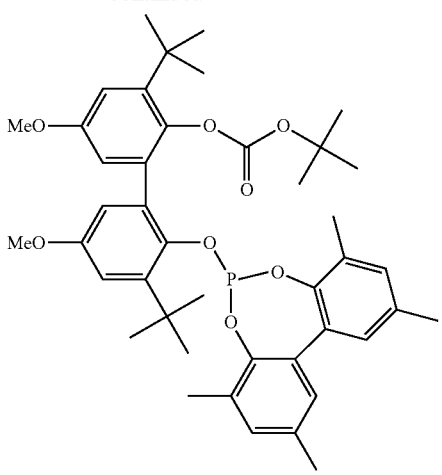 [SMILES: COc1cc(-c2cc(OC)cc(C(C)(C)C)c2Op2oc3c(C)cc(C)cc3c3cc(C)cc(C)c3o2)c(OC(=O)OC(C)(C)C)c(C(C)(C)C)c1]

Introduction of the BOC Group:

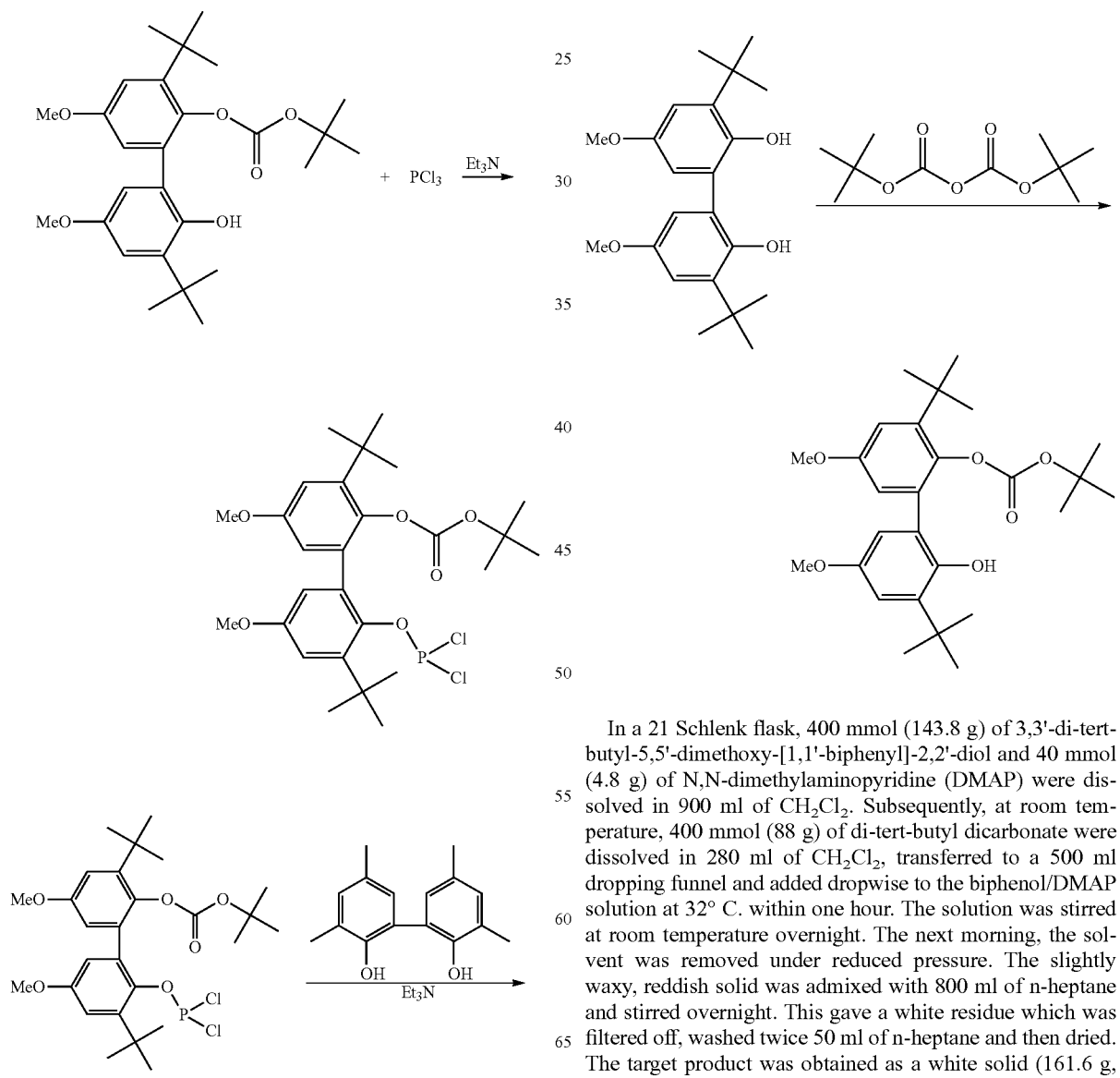

In a 2l Schlenk flask, 400 mmol (143.8 g) of 3,3'-di-tert-butyl-5,5'-dimethoxy-[1,1'-biphenyl]-2,2'-diol and 40 mmol (4.8 g) of N,N-dimethylaminopyridine (DMAP) were dissolved in 900 ml of $CH_2Cl_2$. Subsequently, at room temperature, 400 mmol (88 g) of di-tert-butyl dicarbonate were dissolved in 280 ml of $CH_2Cl_2$, transferred to a 500 ml dropping funnel and added dropwise to the biphenol/DMAP solution at 32° C. within one hour. The solution was stirred at room temperature overnight. The next morning, the solvent was removed under reduced pressure. The slightly waxy, reddish solid was admixed with 800 ml of n-heptane and stirred overnight. This gave a white residue which was filtered off, washed twice 50 ml of n-heptane and then dried. The target product was obtained as a white solid (161.6 g, 84%). $^1$H NMR (toluene-d$_8$): 95% and further impurities.

Reaction of tert-butyl (3,3'-di-tert-butyl-2'-hydroxy-5,5'-dimethoxy-[1,1'-biphenyl]-2-yl)carbonate with phosphorus trichloride

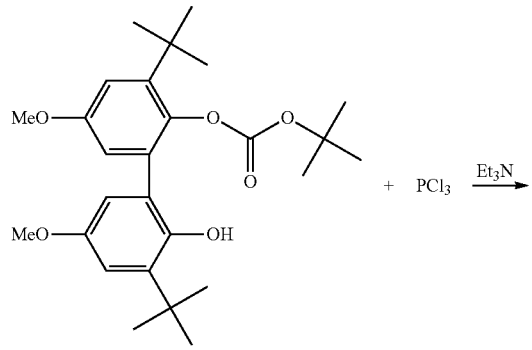

Reaction of tert-butyl (3,3'-di-tert-butyl-2'-((dichlorophosphino)oxy)-5,5'-dimethoxy-[1,1'-biphenyl]-2-yl)-carbonate with 3,3',5,5'-tetramethyl-(1,1'-biphenyl)-2,2'-diol (L1)

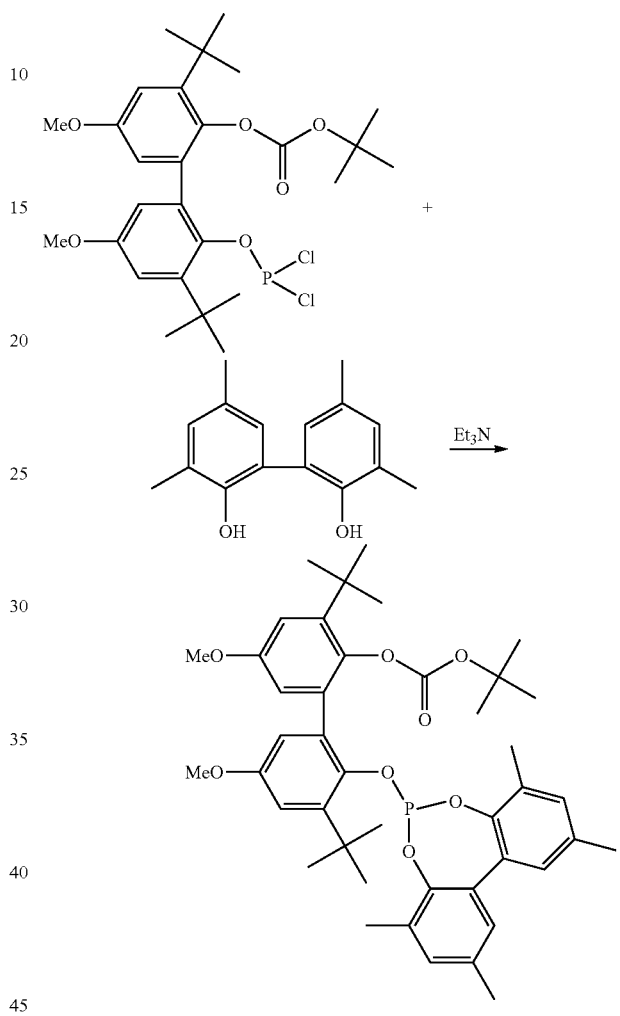

In a 250 ml Schlenk flask which had been repeatedly evacuated and filled with inert gas, 12 g (0.026 mol) of tert-butyl (3,3'-di-tert-butyl-2'-hydroxy-5,5'-dimethoxy-[1,1'-biphenyl]-2-yl)carbonate were dissolved by stirring in 120 ml of dried toluene and 12.8 ml (0.091 mol) of triethylamine.

In a second 500 ml Schlenk flask, 100 ml of dried toluene were first stirred together with 8.1 ml (0.091 mol) of phosphorus trichloride. Subsequently, the phosphorus trichloride-toluene solution was added dropwise to the previously prepared carbonate-amine-toluene solution at room temperature within 30 minutes. On completion of addition, the mixture was heated to 80° C. for 30 minutes and cooled to RT overnight.

The next morning, the mixture was filtered, the solids were washed with 50 ml of dried toluene, and the filtrate was concentrated to dryness. The target product was obtained as a solid (13.1 g, 89%). $^{31}$P NMR (202.4 MHz, toluene-$d_8$): 203.2 and 203.3 ppm (100%).

In a 1 l Schlenk flask which had been repeatedly evacuated and filled with inert gas, 24.7 g (0.044 mol) of tert-butyl (3,3'-di-tert-butyl-2'-((dichlorophosphino)oxy)-5,5'-dimethoxy-[1,1'-biphenyl]-2-yl)-carbonate were dissolved in 400 ml of acetonitrile.

In a second Schlenk flask (1 l) which had been repeatedly evacuated and filled with inert gas, 10.8 g (0.044 mol) of 3,3',5,5'-tetramethyl-(1,1'-biphenyl)-2,2'-diol were dissolved by stirring in 200 ml of acetonitrile and 13.1 ml (0.011 mol) of dried triethylamine. Subsequently, the chlorophosphite solution was slowly added dropwise to the biphenol-triethylamine solution and the mixture was stirred overnight.

The mixture was then filtered and the residue was washed twice with 15 ml of acetonitrile.

The filtrate was concentrated until a solid precipitated out. The latter was filtered and dried. The target product was obtained as a white solid (28.5 g, 87%). $^{31}$P NMR (202.4 MHz, toluene-$d_8$): 139.4 ppm (98.5%).

Reaction of tert-butyl (3,3'-di-tert-butyl-2'-((dichlorophosphino)oxy)-5,5'-dimethoxy-[1,1'-biphenyl]-2-yl)-carbonate with 3,3-di-tert-butyl-5,5-dimethoxy-biphenol (L4)

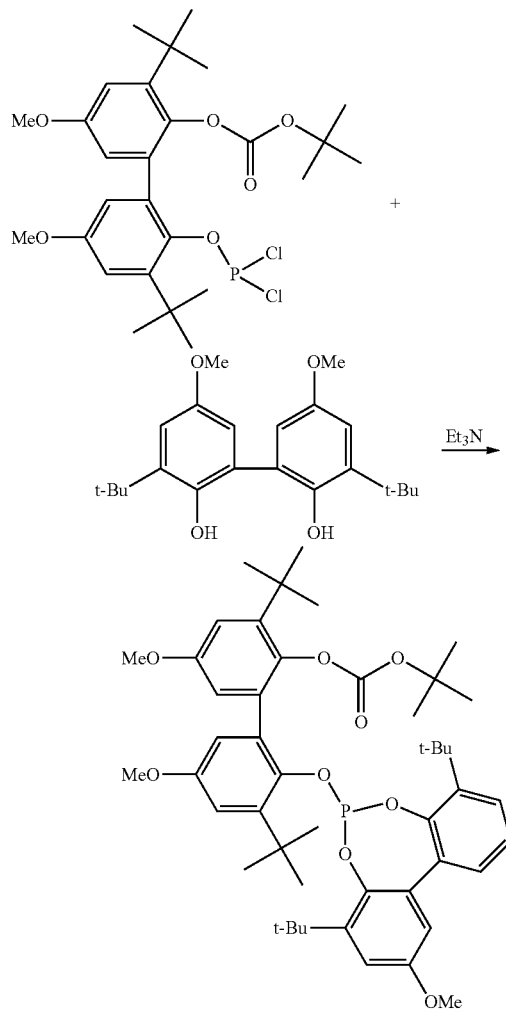

In a 250 ml Schlenk flask which had been repeatedly evacuated and filled with inert gas, 7 g (0.0125 mol) of tert-butyl (3,3'-di-tert-butyl-2'-((dichlorophosphino)oxy)-5,5'-dimethoxy-[1,1'-biphenyl]-2-yl)-carbonate were dissolved in 100 ml of dried acetonitrile.

In a second Schlenk flask (100 ml) which had been repeatedly evacuated and filled with inert gas, 4.5 g (0.0125 mol) of 3,3-di-tert-butyl-5,5-dimethoxybiphenol were dissolved in 60 ml of dried acetonitrile and 4.2 ml (0.03 mol) of degassed triethylamine. Subsequently, the biphenol-triethylamine solution was slowly added dropwise at room temperature to the chlorophosphite solution and the mixture was stirred at room temperature overnight.

A portion of the solvent was removed under reduced pressure. The precipitated solids were filtered off and dried. The target product was obtained as a white solid (10.5 g, 96%). $^{31}$P NMR (202.4 MHz, toluene-$d_8$): 140.9 (95.2%) and further impurities (further impurities=P—H compounds, oxide compounds, as yet incompletely converted chlorophosphite).

Preparation of bis(2,4-di-tert-butyl-6-methylphenyl)ethyl phosphite (L3)

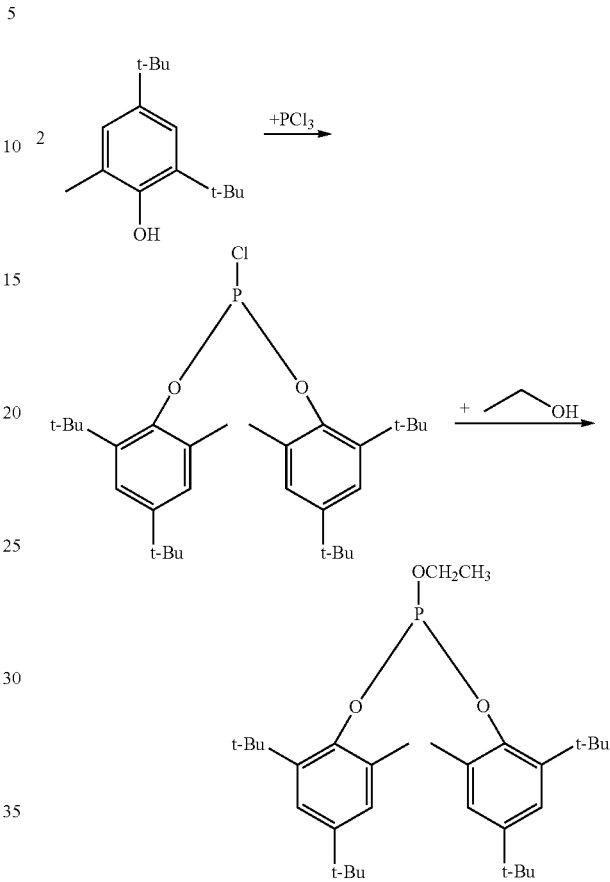

A 250 ml Schlenk flask with magnetic stirrer, attachment, dropping funnel and reflux condenser was initially charged with 22.5 g (0.1 mol) of 2,4-di-tert-butyl-6-methylphenol (4,6-di-tert-butyl-ortho-cresol), and heated to 55° C. in order to melt the phenol. 0.13 ml (0.0015 mol) of dried degassed dimethylformamide was added to the melt. Subsequently, 5.7 ml of phosphorus trichloride (0.065 mol) were added dropwise within 2 hours. After the addition had ended, the reaction mixture was heated to 140° C. within 3 hours and stirred at this temperature for 1 hour. Then the mixture was stirred at 130° C. under reduced pressure for 1 hour. Thereafter, the clear yellow-orange melt obtained (=bis(2,4-di-tert-butyl-6-methyl)phosphochloridite) was cooled down to 80° C. overnight and diluted with 75 ml of degassed petroleum (80-110° C.). After the solution had been cooled down to −5° C., 9.1 ml (0.0665 mol) of degassed triethylamine were added within 15 minutes. Subsequently, within 2 hours, 4.4 ml (0.075 mol) of dried and degassed ethanol were added dropwise, in the course of which the temperature did not rise above 5° C. This mixture was warmed gradually to room temperature overnight while stirring.

The next morning, the precipitated triethylamine hydrochloride was filtered off and the filtrate was concentrated under reduced pressure. This gave a white residue which was recrystallized in 60 ml of degassed ethanol. The product was thus obtained in a yield of 73.9% (19.03 g) as a white solid in 98% purity by LC-MS.

Example 1

This example discloses the determination of the dependence of the controlled variable visc on the mixing ratio of the ligand mixture. Analogously to EP 1430014 B1, this is calculated from the isomer distribution of the product aldehydes of the $C_8$ hydroformylation and reflects an approximate viscosity of the diisononyl phthalate mixture which can be prepared from these aldehydes by hydrogenation and subsequent esterification of the alcohols thus obtained with phthalic acid.

For the determination of the dependence, a number of hydroformylation experiments were conducted by the procedure specified above, using di-n-butene (DnB) with different branching levels. Pressure 50 bar, temperature 140° C., reaction time 180 minutes. The results are shown in Table 3.

TABLE 3

Calculations for Example 1

| No. | Iso index DnB | P/Rh Ligand L1 | P/Rh Ligand L2 | Proportion of L1 [mol-%] | visc [mPas] |
|---|---|---|---|---|---|
| 1 | 1.038 | 19.9 | 0 | 100 | 82.6 |
| 2 | 1.038 | 4.9 | 14.9 | 25 | 88.6 |
| 3 | 1.038 | 0 | 19.8 | 0 | 89.5 |
| 4 | 1.110 | 20.0 | 0 | 100 | 86.6 |
| 5 | 1.110 | 1.9 | 17.1 | 10 | 93.2 |
| 6 | 1.110 | 0 | 19.9 | 0 | 95.6 |
| 7 | 1.151 | 20.3 | 0 | 100 | 87.4 |
| 8 | 1.151 | 5.1 | 15.3 | 25 | 93.0 |
| 9 | 1.151 | 2.0 | 18.1 | 10 | 94.3 |

Figure 2:
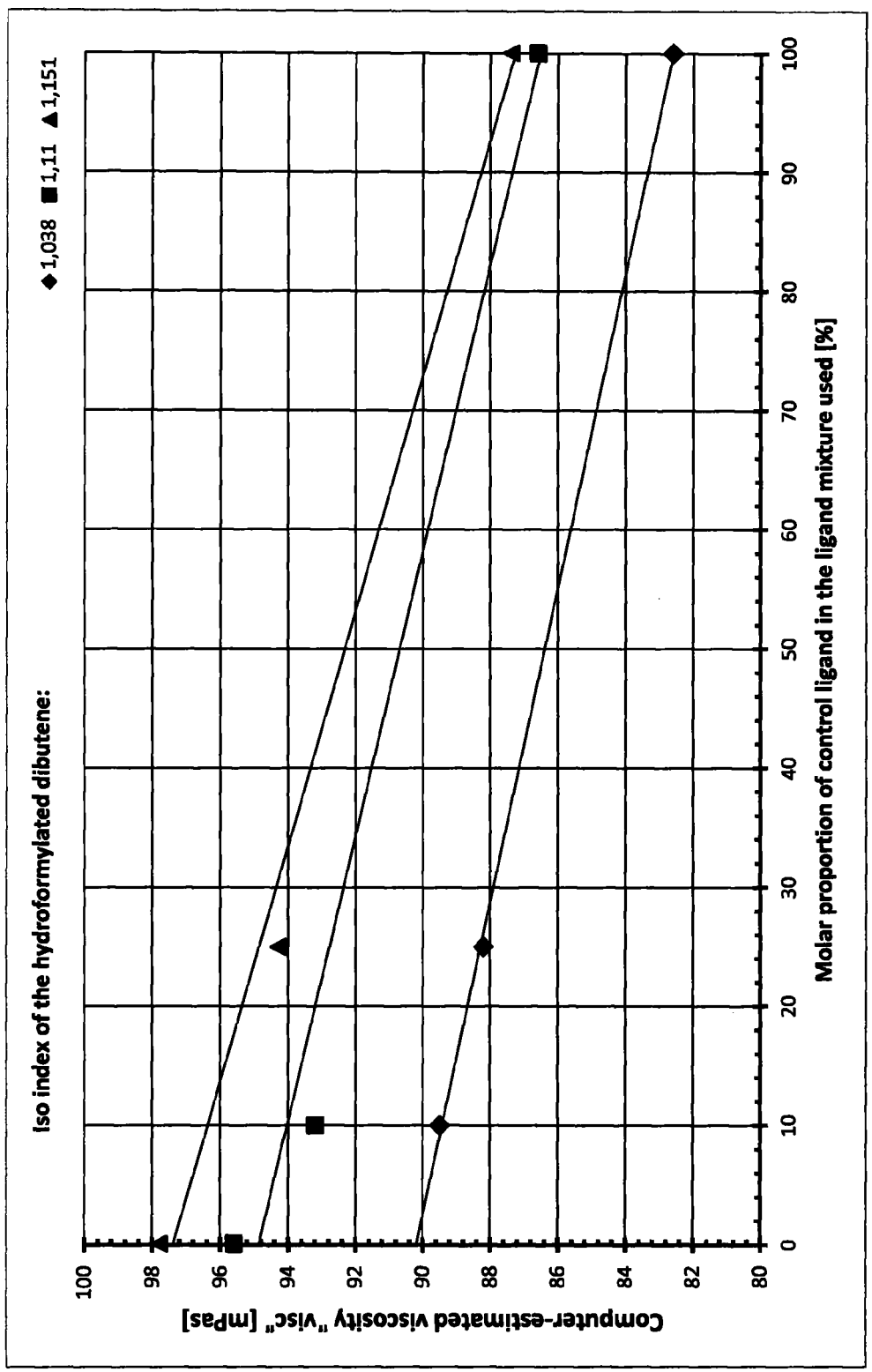
FIG. 2 shows the viscosity of a DINP, calculated from the aldehyde distribution of hydroformylation outputs, as controlled variable viscosity, plotted against the molar proportion of ligand L1 in a mixture of L1 and L2 for various olefin qualities, specified via the iso index.

The results of the experiment are shown in the form of a graph in FIG. 2:

FIG. 2: Viscosity of a DINP, calculated from the aldehyde distribution of hydroformylation outputs, as controlled variable visc, plotted against the molar proportion of ligand L1 in a mixture of L1 and L2 for various olefin qualities, specified via the iso index.

The slope of the regression lines shown in the plot gives the closed-loop control standard for the closed-loop control of the hydroformylation with the aid of the ligand mixture. As can be inferred from FIG. 2, the line slopes in the hydroformylation of di-n-butene mixtures differ only slightly with different iso index, and for that reason it is possible to use the mean of the line slopes here in a good approximation for the closed-loop control. It is $a_1 = -0.087$ mPas/%. This means that, when these two ligands are used, for the mixture, an increase in the proportion of control ligand L1 by 10 percentage points leads to a decrease in the calculated viscosity by 0.87 mPas with constant feedstock and constant reaction conditions in the hydroformylation. If this approximation is inadequate for the closed-loop control, the dependence between visc, the ligand mixture and the iso index of the di-n-butene used has to be described mathematically. For this purpose, the data were plotted again in FIG. 3.

Figure 3:
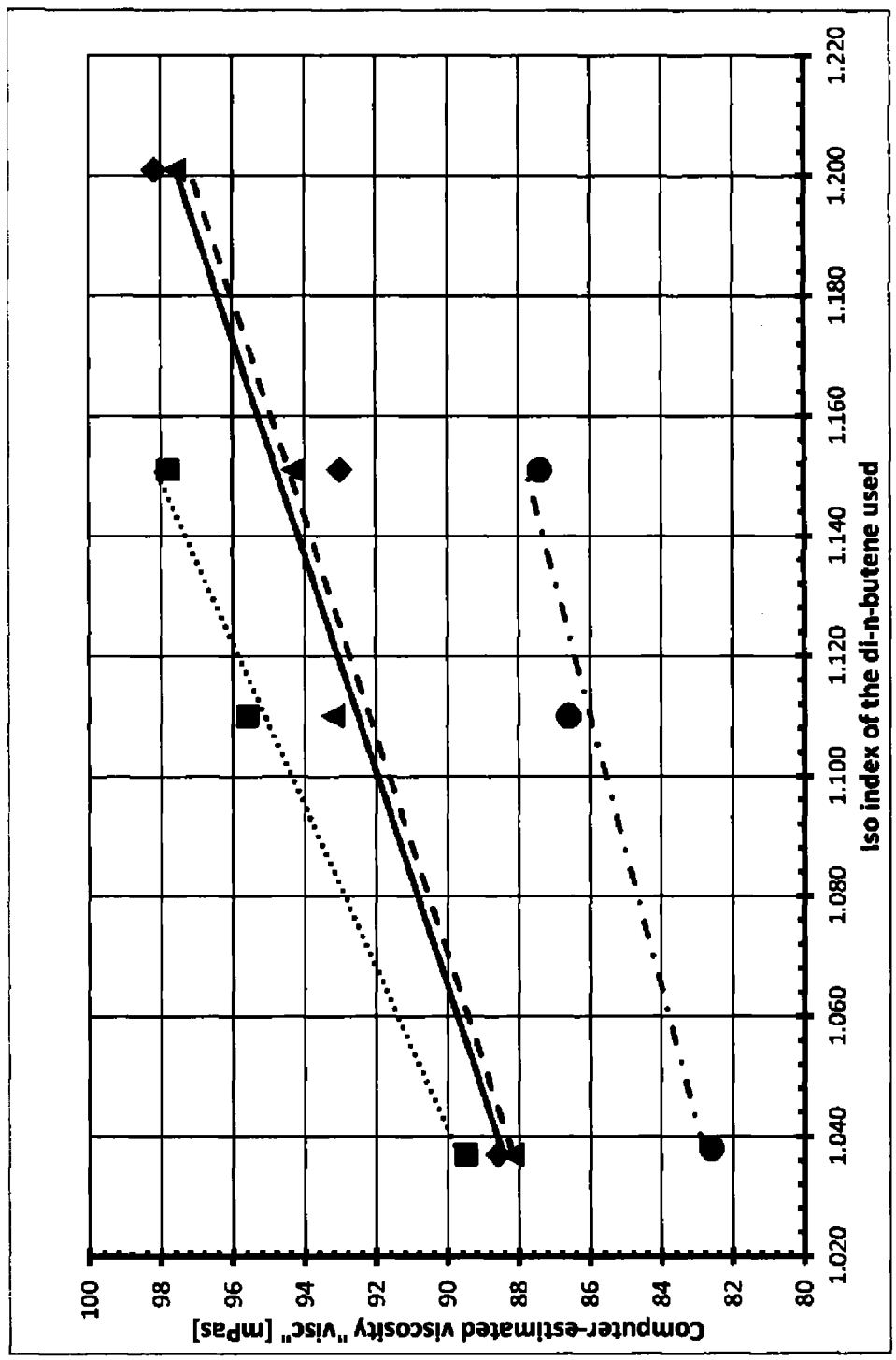
FIG. 3 shows the viscosity of a DINP, calculated from the aldehyde distribution of hydroformylation outputs, as controlled variable viscosity, plotted against the iso index of the di-n-butene used at different mixing ratios.

FIG. 3: Viscosity of a DINP, calculated from the aldehyde distribution of hydroformylation outputs, as controlled variable visc, plotted against the iso index of the di-n-butene used at different mixing ratios.

For the regression lines shown, it is possible to calculate slopes and axis intercepts summarized by Table 4:

TABLE 4

Slopes from the graph in FIG. 3

| Proportion of L1 [mol %] | Natural logarithm of proportion L1 | Slope of the regression lines | Axis intercept of the regression lines |
|---|---|---|---|
| 100 | 4.6051702 | 43.964551 | 37.186982 |
| 25 | 3.2188758 | 55.003774 | 31.124070 |
| 10 | 2.3025851 | 55.692318 | 30.685065 |
| 0.1 | −2.3025851 | 74.062781 | 12.880316 |

Figure 4:
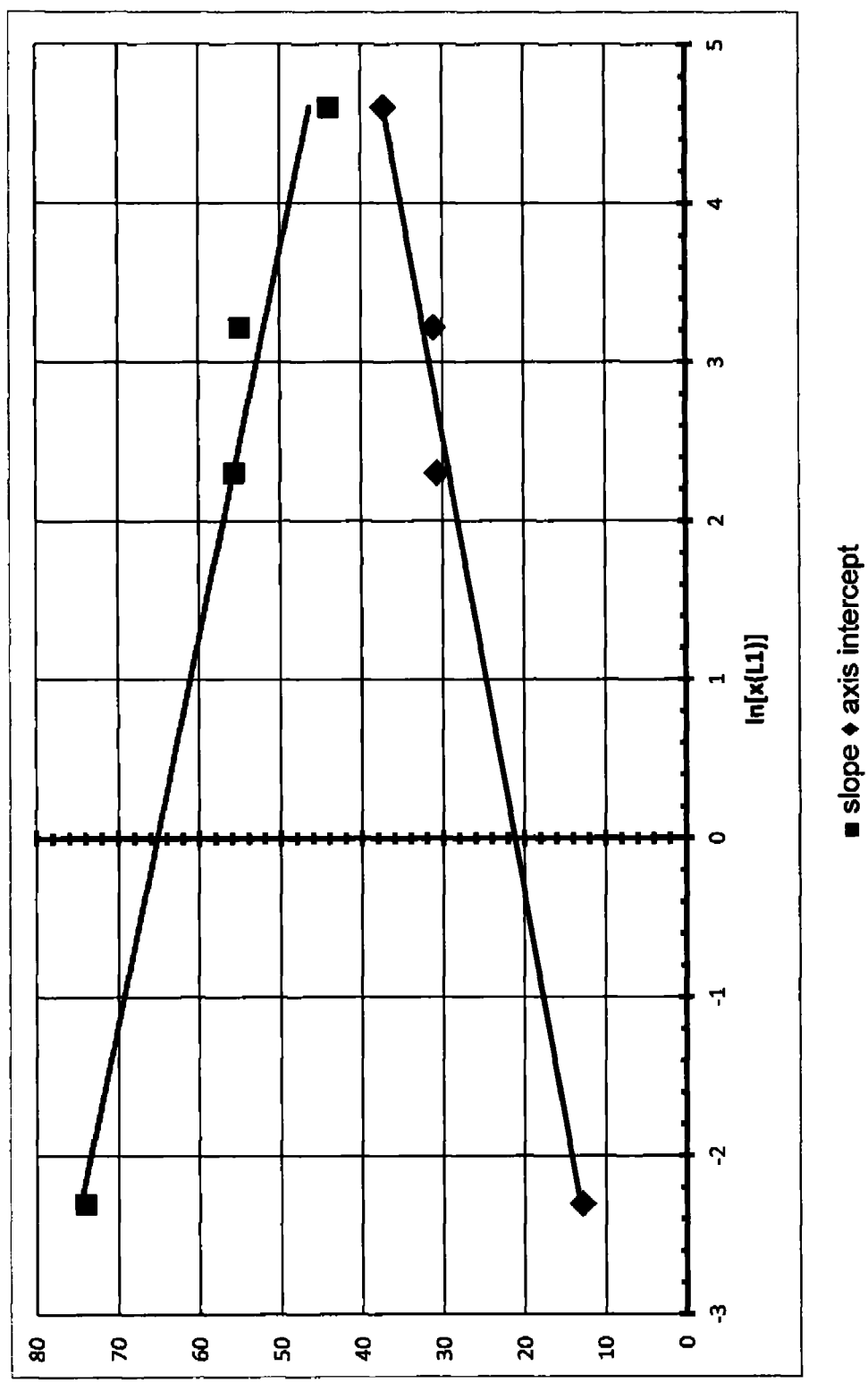
FIG. 4 shows a plot of the slopes and axis intercepts of the regression lines from FIG. 3 against the natural logarithm of the L1 proportion in the ligand mixture.

If the slopes and axis intercepts are plotted against the natural logarithm of the L1 proportion, it is again possible to conduct a linear regression, as shown in FIG. 4.

FIG. 4: Plot of the slopes and axis intercepts of the regression lines from FIG. 3 against the natural logarithm of the L1 proportion in the ligand mixture.

For the two plots, one slope and one axis intercept each are obtained according to Table 5:

TABLE 5

Slopes and axis intercepts from the graph in FIG. 4

| | Slope of the regression lines | Axis intercept of the regression lines |
|---|---|---|
| Plot of the slopes from FIG. 3 | −4.1003453 | 3.4837009 |
| Plot of the axis intercepts from FIG. 3 | 65.201179 | 21.154949 |

Combining the straight-line equations leads to the following dependence of the controlled variable visc on the iso index of the di-n-butene used according to equation (6):

$$visc = \{-4.1003453 \cdot \ln[x(L1)] + 65.201179\} \cdot \left[\frac{iso}{100}\right] + \{3.4837009 \cdot \ln[x(L1)] + 21.154949\} \quad (6)$$

where $x(L1)$ here is the molar proportion of the ligand L1 in the mixture. iso is the controlled variable of the oligomerization which is calculated from the iso index of the dibutene according to equation (7):

$$iso = Isoindex \cdot 100 \quad (7)$$

This equation can be used by a control computer for closed-loop control of the process.

Example 2

Since other control ligands than L1 are also usable in industry, this example determines the dependence when using a mixture of bis(4,6-di-tert-butyl-2-methylphenyl) ethyl phosphite (L3) and L2, and a mixture of L4 and L2. For this purpose, hydroformylation experiments were again conducted, the main results of which can be found in Table 6:

TABLE 6

Calculations for Example 2

| No. | Iso index DnB | P/Rh Ligand L1 | P/Rh Ligand L2 | P/Rh Ligand L3 | P/Rh Ligand L4 | Proportion of control ligand [mol %] | visc [mPas] |
|---|---|---|---|---|---|---|---|
| 10 | 1.038 | 0 | 6.5 | 13.2 | 0 | 67 (L3) | 86.1 |
| 11 | 1.038 | 0 | 10.0 | 10.0 | 0 | 50 (L3) | 86.6 |

TABLE 6-continued

Calculations for Example 2

| No. | Iso index DnB | P/Rh Ligand L1 | P/Rh Ligand L2 | P/Rh Ligand L3 | P/Rh Ligand L4 | Proportion of control ligand [mol %] | visc [mPas] |
|---|---|---|---|---|---|---|---|
| 12 | 1.038 | 0 | 13.3 | 6.5 | 0 | 33 (L3) | 87.3 |
| 13 | 1.038 | 0 | 16.1 | 4.0 | 0 | 20 (L3) | 88.1 |
| 14 | 1.038 | 0 | 4.9 | 0 | 14.9 | 75 (L4) | 87.3 |
| 15 | 1.038 | 0 | 9.9 | 0 | 10.0 | 50 (L4) | 88.6 |
| 16 | 1.038 | 0 | 14.8 | 0 | 4.9 | 25 (L4) | 89.4 |
| 17 | 1.038 | 0 | 18.0 | 0 | 2.1 | 10 (L4) | 89.8 |

Analogous evaluation of these data shows that the proportion of L3 in the mixture with L2, for example, has to be raised by about 11 percentage points in order to achieve a decrease in the calculated viscosity (or in the controlled variable visc) by 0.5 mPas. The proportion of L4 in the mixture with L2 has to be raised by 13 percentage points in order to bring about a decrease by 0.5 mPas. The values apply correspondingly if the viscosity is to be increased.

Example 3

In a further embodiment of the invention, the closed-loop control of the hydroformylation can also be effected via the absolute reaction pressure. For this purpose, a series of hydroformylation experiments were conducted at different reaction pressures. The temperature and reaction time were analogous to Example 1 and 2. The main results are summarized in Table 7:

TABLE 7

Calculations for Example 3

| No. | Iso index DnB | Reaction pressure [bara] | visc [mPas] |
|---|---|---|---|
| 18 | 1.038 | 50 | 79.4 |
| 19 | 1.038 | 100 | 85.8 |
| 20 | 1.038 | 150 | 89.2 |
| 21 | 1.038 | 200 | 93.2 |
| 22 | 1.038 | 235 | 95.4 |

Figure 5:
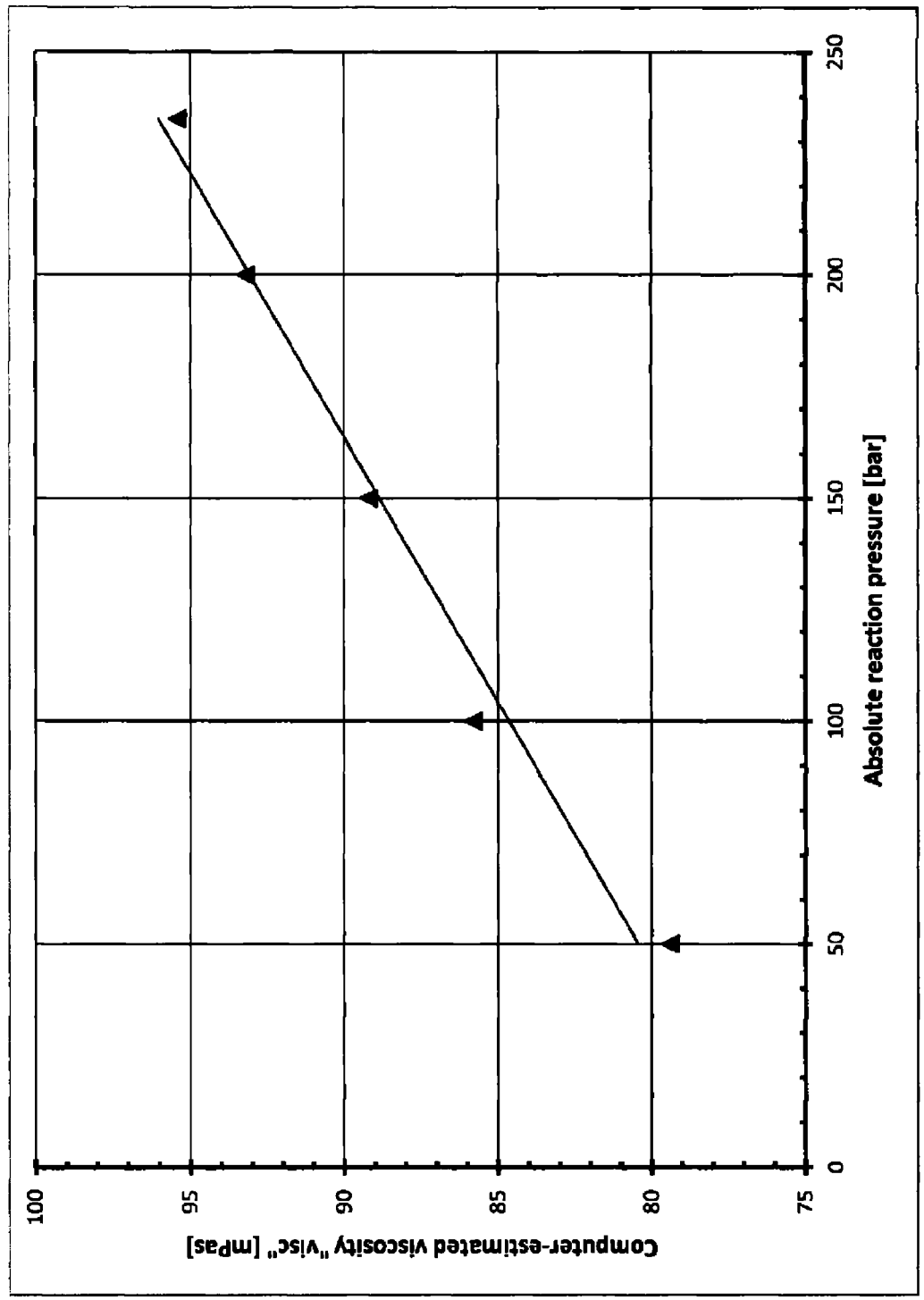
FIG. 5 shows the viscosity of a DINP, calculated from the aldehyde distribution of hydroformylation outputs, as controlled variable viscosity, plotted against the absolute reaction pressure of the hydroformylation reaction which has been conducted in the presence of the ligand L1.

The dependence of the controlled variable visc on the reaction pressure is shown in FIG. 5.

FIG. 5: Viscosity of a DINP, calculated from the aldehyde distribution of hydroformylation outputs, as controlled variable visc, plotted against the absolute reaction pressure of the hydroformylation reaction which has been conducted in the presence of the ligand L1.

The pressure dependence can be derived in an adequate approximation from the slope of the regression lines depicted. Thus, a pressure change by 6 bar leads to a change in the control parameter visc by 0.5 mPas.

Example 4

This example is intended to illustrate the control of a hydroformylation process with the aid of the controlled variable visc. For this purpose, the hydroformylation of a di-n-butene feedstock was conducted. The reaction temperature was set to 140° C. and the reaction pressure to 50 bar. The residence time in the reactor was about 180 minutes. By altering the proportions by mass of base ligand and control ligand in the ligand mixture supplied, it was possible to influence the selectivity of the reaction and hence the DINP viscosity calculated from the aldehyde output. In addition, it is shown how the selectivity of the hydroformylation behaves in the event of variations in the iso index of the di-n-butene used, and how it is possible to produce, with the aid of the controlled variable visc, an aldehyde product with a composition remaining constant within defined limits. Table 8 summarizes important operation points in the campaign of experiments which illustrate the effects of the invention:

TABLE 8

Campaign of experiments from Example 4

| No. | System change or closed-loop control step | Iso index DnB | Proportion of control ligand [mol %] | Yield Aldehyde and alcohol [%] | visc calculated from product of experiment [mPas] | visc from control model [mPas] |
|---|---|---|---|---|---|---|
| 1 | visc < 88 mPas → decrease in proportion of L1 to 2% → then only meter in L2 | 1.038 | 75 | 81.6 | 85.1 | 88.3 ± 1.5 |
| 2 | visc in target range → maintain current ligand ratio (10% L1) → meter in mixture of 10% L1 and 90% L2 changes in feed in the oligomerization → increase in the iso index to 1.151 | 1.038 | 10 | 87.7 | 88.2 | 87.1 ± 1.5 |
| 3 | visc > 94 mPas → increase in L1 to 25% → metered addition of 50% L1 and 50% L2 | 1.151 | 10 | 90.2 | 94.3 | 92.2 ± 1.5 |
| 4 | visc in target range → maintain current ligand ratio (25% L1) → meter in mixture of 25% L1 and 75% L2 | 1.151 | 25 | 88.7 | 93.0 | 92.2 ± 1.5 |

Procedure for Examples 5 to 7

The oligomerization was reworked in a substantially isothermal tubular reactor with the following dimensions: length 4.0 m, internal diameter 32.8 mm. The reactor was equipped with a jacket for thermostat control. The heat carrier used was the Marlotherm product from Sasol. The reaction was conducted at an absolute pressure of 30 bar in the liquid phase. The feedstock used was a hydrocarbon mixture containing the following components which add up to 100% by weight:

1-butene 0-20% by wt.
2-butene 55-75% by wt.
isobutene<1% by wt.
isobutane<2% by wt.
n-butane>24% by wt.

The catalyst used was a material which has been prepared according to Example 1 of WO2011/000697A1 and aftertreated according to Example 4 of the same publication and which had already been in use for more than 2000 hours. In this way, an average operating state of the oligomerization was reworked.

Beyond the reaction stage, the oligomers were separated from the butanes and unconverted butenes and analysed for their composition. For this purpose, for identification of the octene skeletal isomers, hydrogenating GC analysis was used, in which the oligomeric olefins were first hydrogenated to alkanes. The alkanes thus obtained are then separated by gas chromatography and detected. It is possible to differentiate between the three relevant C8 isomers: n-octane (formed from n-octenes), methylheptane (formed from methylheptenes) and dimethylhexane (formed from dimethylhexenes). These values were used to calculate the iso index and these in turn to calculate the controlled variable iso.

A portion of the stream comprising butanes and unconverted butenes was recycled into the upstream reactor. The non-recycled portion of this mixture was disposed of.

In order to reflect the overall process in question, the product discharge (about 500 g) was collected at intervals and subjected to distillative separation in order to separate the desired $C_8$ fraction from the remaining lower-boiling unconverted butenes and butanes and the higher-boiling heavier oligomers and by-products.

Example 5

For the design of the closed-loop control, a single experimental determination of the dependences between the controlled variable iso and the parameters of temperature and recycle rate is necessary. In the case of the oligomerization, determination was conducted on the basis of a statistical plan of experiments which was compiled with the aid of the computer program MiniTab. On the basis of this plan of experiments, the necessary changes in parameters were undertaken in the pilot plant. After each change, there was a wait period until the reaction system was in the steady state again. Then the sampling was conducted. The parameter range for the plan of experiments was limited by the technical features of the plant. Thus, it was only possible to establish temperatures between 45 and 60° C., since the reaction becomes too slow at lower temperatures and rapid deactivation of the catalyst can occur at higher temperatures. The amount of recyclable butene/butane stream can be varied from 0 to 400 grams per hour. The composition of the raw material stream was set arbitrarily to 0.6% to 40% by mass of 1-butene, and the required compositions were made up in a controlled manner.

The plan of experiments and the results obtained are compiled in Table 9.

TABLE 9

Plan of experiments and results for Example 5

| Std. seq. | Run seq. | Point type | Blocks | Temp. [° C.] | Reflux [kg/h+] | Conc. of 1-butene [% by mass] | Conversion [%] | S(C8) [%] | Proportion of nO | Proportion of MH | Proportion of DMH | Iso index |
|---|---|---|---|---|---|---|---|---|---|---|---|---|
| 15 | 1 | 0 | 1 | 52.5 | 0.20 | 20.3 | 73.6 | 81.5 | 0.150 | 0.654 | 0.196 | 1.046 |
| 10 | 2 | −1 | 1 | 60.0 | 0.20 | 20.3 | 83.4 | 79.0 | 0.150 | 0.645 | 0.204 | 1.054 |
| 1 | 3 | 1 | 1 | 48.0 | 0.08 | 8.6 | 61.4 | 81.5 | 0.146 | 0.648 | 0.206 | 1.059 |
| 20 | 4 | 0 | 1 | 52.5 | 0.20 | 20.3 | 73.6 | 81.5 | 0.150 | 0.654 | 0.196 | 1.046 |
| 3 | 5 | 1 | 1 | 48.0 | 0.32 | 8.6 | 67.8 | 84.3 | 0.145 | 0.656 | 0.199 | 1.054 |
| 14 | 6 | −1 | 1 | 52.5 | 0.20 | 40.0 | 74.4 | 81.3 | 0.151 | 0.661 | 0.187 | 1.036 |
| 6 | 7 | 1 | 1 | 57.0 | 0.08 | 32.0 | 78.5 | 78.0 | 0.154 | 0.652 | 0.194 | 1.040 |
| 13 | 8 | −1 | 1 | 52.5 | 0.20 | 0.6 | 73.6 | 81.5 | 0.143 | 0.628 | 0.229 | 1.085 |
| 8 | 9 | 1 | 1 | 57.0 | 0.32 | 32.0 | 81.5 | 81.3 | 0.150 | 0.657 | 0.192 | 1.042 |
| 18 | 10 | 0 | 1 | 52.5 | 0.20 | 20.3 | 73.6 | 81.5 | 0.150 | 0.654 | 0.196 | 1.046 |
| 12 | 11 | −1 | 1 | 52.5 | 0.40 | 20.3 | 76.6 | 83.4 | 0.148 | 0.659 | 0.194 | 1.046 |
| 2 | 12 | 1 | 1 | 57.0 | 0.08 | 8.6 | 77.9 | 78.1 | 0.148 | 0.628 | 0.223 | 1.075 |
| 17 | 13 | 0 | 1 | 52.5 | 0.20 | 20.3 | 73.6 | 81.5 | 0.150 | 0.654 | 0.196 | 1.046 |
| 9 | 14 | −1 | 1 | 45.0 | 0.20 | 20.3 | 59.4 | 84.2 | 0.146 | 0.663 | 0.191 | 1.045 |
| 4 | 15 | 1 | 1 | 57.0 | 0.32 | 8.6 | 81.3 | 81.3 | 0.146 | 0.642 | 0.211 | 1.065 |
| 16 | 16 | 0 | 1 | 52.5 | 0.20 | 20.3 | 73.6 | 81.5 | 0.150 | 0.654 | 0.196 | 1.046 |
| 19 | 17 | 0 | 1 | 52.5 | 0.20 | 20.3 | 73.6 | 81.5 | 0.150 | 0.654 | 0.196 | 1.046 |
| 7 | 18 | 1 | 1 | 48.0 | 0.32 | 32.0 | 68.7 | 84.1 | 0.148 | 0.665 | 0.187 | 1.040 |
| 5 | 19 | 1 | 1 | 48.0 | 0.08 | 32.0 | 49.9 | 83.7 | 0.147 | 0.667 | 0.186 | 1.039 |
| 11 | 20 | −1 | 1 | 52.5 | 0.00 | 20.3 | 68.0 | 77.8 | 0.152 | 0.648 | 0.199 | 1.047 |

Std. seq. = standard sequence; Run seq. = run sequence; Temp. = temperature; Conc. = concentration; S(C8) = selectivity for di-n-butene The experimental data thus obtained were evaluated by the methods of statistical design of experiments. A comprehensive introduction into the methods of design of experiments is given, for example, by Ž. R. Lazić, Design of Experiments in Chemical Engineering, Wiley-VCH, 2004.

For this purpose, the computer program MiniTab was likewise used, with the aid of which what is called an effective area of the different parameters was calculated. The output of the program gives information according to Tables 10 and 11:

TABLE 10

Results for the iso index

| Term | Coefficient |
|---|---|
| Constant | 113.814 |
| Temperature | −0.360474 |
| Reflux | −4.36236 |
| Butene conc | −0.00618174 |
| Temperature * temperature | 0.00518875 |
| Butene conc. * butene conc | 0.00364209 |
| Temperature * butene conc | −0.00545420 |
| Reflux * butene conc | 0.174800 |

TABLE 11

Results for the conversion

| Term | Coefficient |
|---|---|
| Constant | −181.465 |
| Temperature | 7.52134 |
| Reflux | 237.263 |
| Butene conc. | −1.70002 |
| Temperature * temperature | −0.0510611 |
| Temperature * reflux | −4.39695 |
| Temperature * butene conc | 0.0272597 |
| Reflux * butene conc. | 1.08140 |

With the aid of the terms and coefficients, it is possible to formulate the description of the effective area using the following two equations (3) and (4):

$$\text{iso}=113.814-0.360474\cdot T-4.36236\cdot R-0.0618174\cdot w(1-B)+0.00518875\cdot T^2+0.0364209\cdot w^2(1-B)-0.00545420\cdot T\cdot w(1-B)+0.174800\cdot R^2 \quad (3)$$

$$\text{conv}=-181.465+7.52134\cdot T+237.263\cdot R-1.70002\cdot w(1-B)-0.0510611\cdot T^2-4.39695\cdot T\cdot R+0.0272597\cdot T\cdot w(1-B)+1.08140\cdot R\cdot w(1-B) \quad (4)$$

where iso and cony are the controlled variables specified in FIG. 1. T represents the temperature (in degrees Celsius) of the heat carrier with which the temperature of the oligomerization reactor is controlled, R indicates the recycle rate of unconverted butenes (based on the experiments, reported in kg/h) and w(1−B) indicates the proportion by mass of 1-butene in the $C_4$ hydrocarbon stream used.

Example 6

This example is intended to describe closed-loop control of the oligomerization using the parameters iso and cony. The experiments were conducted in the same plant as those in Example 5. Since the pilot plant available was equipped only with manual regulators, the closed-loop control here was implemented in such a way that the equation systems for the closed-loop control were first programmed into a control computer. This computer also collected the analysis results and other measured data, some automatically and some manually (operator input). The computer was subject to particular provisos, for example that the conversion is to be increased to at least 80% or that the iso index of the product is to lie between 1.045 and 1.050. Based on these provisos, the control software produced control instructions (for example raise temperature to at least 57° C.), which were then read off by an operator and programmed into the manual regulators of the plant.

The results are shown in Table 12.

TABLE 12

Results for Example 6

| No. | System change or closed-loop control step | 1-Butene content in feed [% by mass] | Temp. [° C.] | Reflux of unconverted butenes [kg/h] | Conversion of butenes [%] | Iso index calculated from product | iso or conv from formula 3 or 4 |
|---|---|---|---|---|---|---|---|
| 1 | Increase in conversion desired → raise the temperature → target parameter conv > 80 | 24.7 | 50 target >= 57 | 0.2 | 69.6 | 1.042 | 104.1 67.5 104.5 80.4 |
| 2 | Lowering of the iso index, desired at conversion > 80% → lower the temperature, raise the reflux → target parameters 80 < conv < 84, iso <= 104.5 | 24.7 | 60 target~55 | 0.2 target >= 0.3 | 83.6 | 1.049 | 104.8 84.4 104.3 79.5 |
| 3 | Addition of a low-1-butene C4 stream → lower the 1-butene concentration | 24.7 | 55 | 0.4 | 80.1 | 1.045 | 104.3 81.4 |
| 4 | Lowering of the iso index desired → lower the temperature, adjust the reflux → 4 target parameter iso <= 105.0 | 10.2 | 55 target <= 47 | 0.4 target >= 0.4 | 79.8 | 1.058 | 105.9 78.3 105.0 71.6 |
| 5 |  | 10.2 | 45 | 0.4 | 68.9 | 1.050 | 104.9 68.9 |

Example 7

The example which follows is intended to show that it is particularly advantageous when the component processes of oligomerization and hydroformylation are not viewed separately from one another, but as a process unit which can be controlled jointly with the aid of few parameters such as iso and vise.

For this purpose, the oligomerization was conducted as described above and the di-n-butene product was freed of higher- and lower-boiling impurities by distillation and provided for the hydroformylation. The dibutene provided was analysed as described above to determine the iso index. Then the dibutene was hydroformylated as described above and the product aldehydes obtained were analysed by gas chromatography in order to ascertain the aldehyde distribution, from which the control variable vise was calculated. The measurement and analysis data were collected on a control computer and evaluated with the aid of the above-derived interaction functions. On the basis of particular boundary parameters (parameter limits of oligomerization and hydroformylation, and also arbitrary $C_4$ feedstock mixtures and upper and lower limits for the calculated DINP viscosity), the computer produced control instructions for the hydroformylation and oligomerization which were set in the pilot plants by an operator. After establishing steady states, the plants were sampled. On the basis of the results, the success of the closed-loop control was checked and the next control step was executed. The results are shown in Table 13.

TABLE 13

Experimental results for Example 7

| No. | System change or requirements | Control instruction for oligo-merization | 1-Butene content in feed [% by mass] | Temp. [° C.] | Reflux of un-converted butenes [kg/h] | Con-version of butenes [%] | Iso index from product | iso or conv from formula 3 or 4 | Control in-struction for hydro-formylation | Pro-portion of control ligand L1 [mol %] | visc calculated from product of ex-periment [mPas] | visc from control model [mPas] |
|---|---|---|---|---|---|---|---|---|---|---|---|---|
| 1 | Boundary conditions | visc >= 90 conv >= 80 | 0.6-40 10.2 | 45-60 45 target >= 59 | 0-0.4 0.4 target <= 0.2 | 68.9 | 1.050 | 107.1 81.3 | | 10 | 90-92 89.2 | |
| 2 | 1-butene 10.2→0.6% | | 10.2 | 60 | 0.1 | 82.3 | 1.075 | | | 10 | 90.6 | |
| 3 | | visc <= 92 conv >= 80 | 0.6 | 60 target 60 | 0.1 target 0.2-0.3 | 83.5 | 1.136 | 109.4 | | 10 | 94.0 | → 90.2 |
| 4 | | | 0.6 | 60 | 0.2 | 84.1 | 1.113 | | visc <= 92 | 10 target 25 | 93.2 | target <= 92 |
| 5 | | visc <= 90 conv~80 | 0.6 | 60 target 55 | 0.2 target 0.4 | 84.1 | 1.113 | 107.8 | | 25 | 92.3 | → 88.4 |
| 6 | 1-butene 0.6→10.2% | | 0.6 | 55 | 0.4 | 79.9 | 1.077 | | | 25 | 90.4 | |
| 7 | | | 10.2 | 55 | 0.4 | 79.8 | 1.058 | | visc >= 90 | 25 target 0.1 | 89.3 | <= 92 |
| 8 | 1-butene 10.2→24.7% | | 10.2 | 55 | 0.4 | 79.8 | 1.058 | | | 0.1 | 91.2 | |
| 9 | | | 24.7 | 55 | 0.4 | 80.1 | 1.045 | | | 0.1 | 90.3 | |

German patent application 102014209536.0 filed May 20, 2014, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A process for continuously preparing an alcohol mixture, said process comprising:
   oligomerizing an input mixture, which comprises an olefin and has a composition that changes over time, to obtain an oligomerizate comprising olefin oligomers;
   hydroformylating at least a portion of the olefin oligomers present in the oligomerizate with carbon monoxide and hydrogen in the presence of a homogeneous catalyst system comprising rhodium and at least two different monophosphite ligands to give aldehydes; and
   subsequently hydrogenating at least a portion of the aldehydes to obtain said alcohol mixture;
   wherein
   a composition of the oligomerizate and a composition of the aldehydes are determined during said process,
   a temperature and/or a conversion in the oligomerization are controlled as a function of a current composition of the oligomerizate, and
   a composition of the catalyst system during the hydroformylating is controlled by metered addition of one of the at least two monophosphite ligands into the hydroformylation as a function of a current composition of the aldehydes.

2. The process according to claim 1, wherein the composition of the oligomerizate and the composition of the aldehydes are determined continuously, and the oligomerizing and/or the hydroformylating are controlled continuously.

3. The process according to claim 1, wherein at least the hydroformylating is controlled in such a way that a first scalar controlled variable calculated from the composition of the aldehydes is kept constant.

4. The process according to claim 3, wherein the oligomerizing is controlled in such a way that the first scalar controlled variable calculated from the composition of the aldehydes is kept constant.

5. The process according to claim 3, wherein the first scalar controlled variable is an approximation of the viscosity of an ester mixture obtained by esterification of the alcohol mixture or by transesterification with the aid of the alcohol mixture.

6. The process according to claim 1, wherein the oligomerizing is controlled in such a way that a second scalar controlled variable calculated from the composition of the olefin oligomers is kept constant.

7. The process according to claim 6, wherein the second scalar controlled variable is an approximation of the iso index of the oligomerizate.

8. The process according to claim 1, wherein the input mixture comprises an olefin having four carbon atoms which is oligomerized in the course of the oligomerization to give olefin oligomers having eight, twelve and sixteen carbon atoms, and the olefin oligomers having eight carbon atoms are removed from the oligomerizate and hydroformylated to aldehydes having nine carbon atoms.

9. The process according to claim 8, wherein the input mixture comprises a combination of the following compound mass flow rates which vary within the specified compound mass flow rate ranges with a respective rate of variation within the specified range of rates of variation:

| compound | compound mass flow rate | Rate of variation |
| --- | --- | --- |
| isobutene: | 0 kg/s to 1 kg/s | −0.05 g/s² to 0.05 g/s² |
| 1-butene: | 0 kg/s to 6 kg/s | −0.30 g/s² to 0.30 g/s² |
| 2-butene (cis + trans): | 1 kg/s to 13 kg/s | −0.30 g/s² to 0.30 g/s² |
| isobutane: | 0 kg/s to 3 kg/s | −0.15 g/s² to 0.15 g/s² |
| n-butane: | 1 kg/s to 7 kg/s | −0.30 g/s² to 0.30 g/s² |
| other materials: | 0 kg/s to 1 kg/s | −0.05 g/s² to 0.05 g/s². |

10. The process according to claim 1, wherein the oligomerizing is effected in the presence of a heterogeneous nickel catalyst.

11. The process according to claim 1, wherein the oligomerization is operated in circulation mode, in such a way that a proportion of the oligomerizate drawn off from the oligomerization is recycled into the oligomerization, wherein
a conversion of said input mixture in the oligomerization is controlled by varying the proportion of an oligomerizate recycled.

12. The process according to claim 1, wherein the one monophosphite ligand is metered in such a way that the molar ratio of the sum total of all the monophosphite ligands to rhodium remains constant, taking account of ligand losses.

13. The process according to claim 1, wherein the homogeneous catalyst system comprises exactly two different monophosphite ligands, the first monophosphite ligand being a compound of structural formula II, and
wherein the second monophosphite ligand is a compound of structural formula Ia, Ib or III:

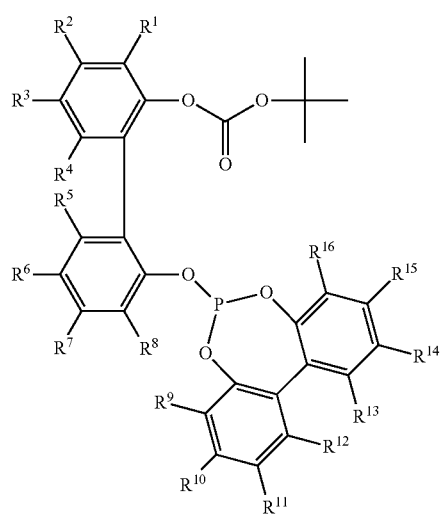

Ia wherein, in Ia,
$R^1$, $R^2$, $R^3$, $R^4$, $R^5$, $R^6$, $R^7$, $R^8$ are each independently selected from the group consisting of:

—H, —($C_1$-$C_{12}$ alkyl), —O—($C_1$-$C_{12}$ alkyl), —O—($C_6$-$C_{20}$ aryl), —($C_6$-$C_{20}$ aryl), halogen, —COO—($C_1$-$C_{12}$ alkyl), —CONH—($C_1$-$C_{12}$ alkyl), —($C_6$-$C_{20}$ aryl)-CON[($C_1$-$C_{12}$ alkyl)]$_2$, —CO—($C_1$-$C_{12}$ alkyl), —CO—($C_6$-$C_{20}$ aryl), —COOH, —OH, —$SO_3H$, —$SO_3Na$, —$NO_2$, —CN, —$NH_2$, and —N[($C_1$-$C_{12}$ alkyl)]$_2$; and $R^9$, $R^{10}$, $R^{11}$, $R^{12}$, $R^{13}$, $R^{14}$, $R^{15}$, $R^{16}$ are each independently selected from the group consisting of:

—H, —($C_1$-$C_{12}$ alkyl), —O—($C_1$-$C_{12}$ alkyl), —O—($C_6$-$C_{20}$ aryl), —($C_6$-$C_{20}$ aryl), halogen, —COO—($C_1$-$C_{12}$ alkyl), —CONH—($C_1$-$C_{12}$ alkyl), —($C_6$-$C_{20}$ aryl)-CON[($C_1$-$C_{12}$ alkyl)]$_2$, —CO—($C_1$-$C_{12}$ alkyl), —CO—($C_6$-$C_{20}$ aryl), —COOH, —OH, —$SO_3H$, —$SO_3Na$, —$NO_2$, —CN, —$NH_2$, and —N[($C_1$-$C_{12}$ alkyl)]$_2$

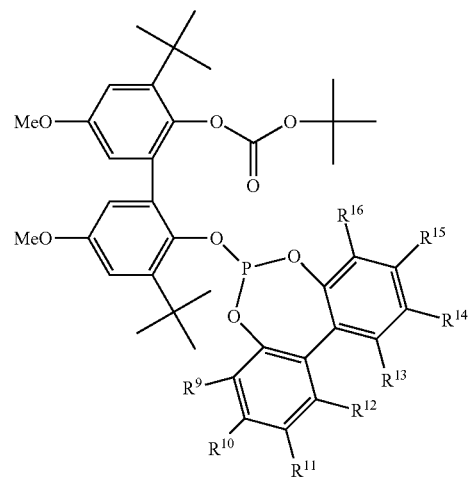

Ib wherein, in Ib,
$R^9$, $R^{10}$, $R^{11}$, $R^{12}$, $R^{13}$, $R^{14}$, $R^{15}$, $R^{16}$ are each independently selected from the group consisting of:

—H, —($C_1$-$C_{12}$ alkyl), —O—($C_1$-$C_{12}$ alkyl), —O—($C_6$-$C_{20}$ aryl), —($C_6$-$C_{20}$ aryl), halogen, —COO—($C_1$-$C_{12}$ alkyl), —CONH—($C_1$-$C_{12}$ alkyl), —($C_6$-$C_{20}$ aryl)-CON[($C_1$-$C_{12}$ alkyl)]$_2$, —CO—($C_1$-$C_{12}$ alkyl), —CO—($C_6$-$C_{20}$ aryl), —COOH, —OH, —$SO_3H$, —$SO_3Na$, —$NO_2$, —CN, —$NH_2$, and —N[($C_1$-$C_{12}$ alkyl)]$_2$

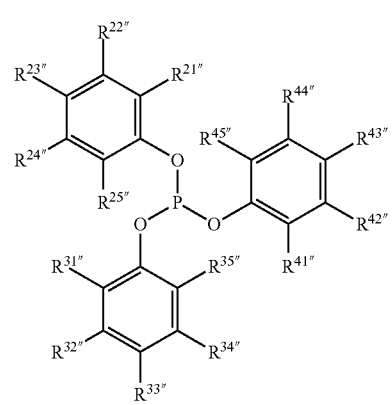

II wherein, in II,
$R^{21''}, R^{22''}, R^{23''}, R^{24''}, R^{25''}, R^{31''}, R^{32''}, R^{33''}, R^{34''}, R^{35''}, R^{41''}, R^{42''}, R^{43''}, R^{44''}, R^{45''}$ are each independently selected from the group consisting of:
—H, —($C_1$-$C_{12}$ alkyl), —O—($C_1$-$C_{12}$ alkyl), —O—($C_6$-$C_{20}$ aryl), —($C_6$-$C_{20}$aryl), halogen, —COO—($C_1$-$C_{12}$ alkyl), —CONH—($C_1$-$C_{12}$ alkyl), —($C_6$-$C_{20}$ aryl)-CON[($C_1$-$C_{12}$ alkyl)]$_2$, —CO—($C_1$-$C_{12}$ alkyl), —CO—($C_6$-$C_{20}$ aryl), —COOH, —OH, —$SO_3H$, —$SO_3Na$, —$NO_2$, —CN, —$NH_2$, and —N[($C_1$-$C_{12}$ alkyl)]$_2$

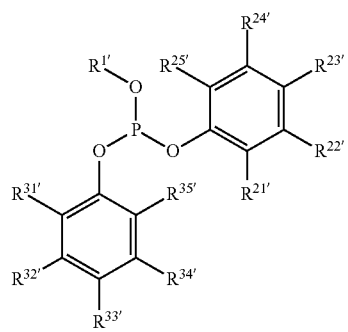

III wherein, in III,
$R^{1'}$ is selected from the group consisting of —($C_1$-$C_{12}$ alkyl), and —($C_3$-$C_{12}$ cycloalkyl), and $R^{21'}, R^{22'}, R^{23'}, R^{24'}, R^{25'}, R^{31'}, R^{32'}, R^{33'}, R^{34'}, R^{35'}$ are each independently selected from the group consisting of:
—H, —($C_1$-$C_{12}$ alkyl), —O—($C_1$-$C_{12}$ alkyl), —O—($C_6$-$C_{20}$ aryl), —($C_6$-$C_{20}$ aryl), -halogen, —COO—($C_1$-$C_{12}$ alkyl), —CO—($C_1$-$C_{12}$ alkyl), —CO—($C_6$-$C_{20}$ aryl), —COOH, and —OH.

14. The process according to claim 13, wherein the second monophosphite ligand is a compound of structural formula Ia or Ib.

15. The process according to claim 13, wherein the second monophosphite ligand is a compound of structural formula Ia.

16. The process according to claim 13, wherein the second monophosphite ligand is a compound of structural formula Ib.

17. The process according to claim 1, wherein a pressure during the hydroformylating is controlled, in addition to the composition of the catalyst system, as a function of a current composition of the aldehydes.

18. The process according to claim 1, further comprising:
esterifying said alcohol mixture with an acid, to obtain an ester mixture.

19. The process according to claim 18, wherein said ester mixture is a plasticizer.

* * * * *